(12) United States Patent
Jiang

(10) Patent No.: US 7,247,716 B2
(45) Date of Patent: Jul. 24, 2007

(54) RECOMBINANT SEQUENCE, ITS PREPARATION AND USE

(75) Inventor: Wen G Jiang, Heath Park (GB)

(73) Assignee: University College Cardiff Consultants Limited, Cardiff (GB)

( * ) Notice: Subject to any disclaimer, the term of this patent is extended or adjusted under 35 U.S.C. 154(b) by 308 days.

(21) Appl. No.: 10/275,296

(22) PCT Filed: May 4, 2001

(86) PCT No.: PCT/GB01/01956

§ 371 (c)(1),
(2), (4) Date: Jun. 9, 2003

(87) PCT Pub. No.: WO01/83562

PCT Pub. Date: Nov. 8, 2001

(65) Prior Publication Data

US 2004/0253239 A1    Dec. 16, 2004

(30) Foreign Application Priority Data

May 4, 2000    (GB) .................................. 0010630

(51) Int. Cl.
*C07H 21/04*    (2006.01)
*A61K 31/713*    (2006.01)
*C12N 5/00*    (2006.01)
*C12N 1/00*    (2006.01)
*C12N 15/00*    (2006.01)

(52) U.S. Cl. ..................... 536/23.4; 435/325; 435/243; 435/320.1; 514/44

(58) Field of Classification Search ..................... None
See application file for complete search history.

(56) References Cited

FOREIGN PATENT DOCUMENTS

| | | |
|---|---|---|
| WO | WO 98 25946 | 6/1998 |
| WO | WO 00 02902 | 1/2000 |

OTHER PUBLICATIONS

Bachelot et al:, "Retrovirus-mediated gene transfer of an angiostatin-endostatin fusion protein with enhanced anti-tumor properties in vivo", Proceedings of the 89th. Annual Meeting of the American Association for Cancer Research. New Orleans, LA, Mar. 28-Apr. 1, 1998, Proceedings of the Annual Meeting of the American Association for Cancer Research, Philadelphia, PA: AACR, US, vol. 39, Mar. 1, 1998 p. 271 XP002089298 the whole document.
S Hiscox et al., "Inhibition of HGF/SF-Induced Breast Cancer Cell Motility and Invasion by the HGF/SF Variant, NK4" Breast Cancer Research and Treatment, Nijhoff, Boston, US, vol. 59, No. 3, Feb. 2000, pp. 245-254, XP001018101 ISSN: 0167-6806 the whole document.
M. Maemondo et al:, "Intratumoral Delivery of Hepatocyte Growth Factor Antagonist (HGF/NK4) Gene by Adenoviral Vector Suppresses the Tumor Growth of Human Lung Cancers In Vivo", Proceedings of the Annual Meeting of the American Association for Cancer Research, New York NY, US, No. 41, Mar. 2000, p. 605 XP001019062 ISSN: 0197-016X the whole document.
Melanie R. Mark et al:, "Expression and characterization of hepatocyte growth factor receptor-IgG fusion proteins: Effects of mutations in the potential proteolytic cleavage site on processing and ligand binding", Journal of Biological Chemistry, vol. 267, No. 36, 1992, pp. 26166-26171, XO002106575 ISSN: 0021-9258 the whole document.

*Primary Examiner*—Scott D. Priebe
*Assistant Examiner*—Michael Burkhart
(74) *Attorney, Agent, or Firm*—Young & Thompson

(57) ABSTRACT

An isolated, purified or recombinant nucleic acid sequence is disclosed, comprising: (a) a sequence that encodes both an angiogenic factor antagonist and a vascular endothelial structure regulator; (b) a sequence substantially homologous to or that hybridizes to sequence (a) under stringent conditions; or (c) a sequence substantially homologous to or that hybridizes under stringent conditions to the sequence (a) or (b) but for the degeneracy of the genetic code; or (g) an oligonucleotide specific for any of the sequences (a), (b) or (c). Particular oligonucleotides (d) are those encoding the vascular endothelial structure regulator. Also described are methods for preparing the recombinant polynucleotide, proteins encoded by such polynucleotides and their use in gene or protein therapy for the treatment of conditions such as cancer.

5 Claims, 13 Drawing Sheets

Figure 1

```
ATAGATCCAG CACTGAAGAT AAAAACCAAA AAAGTGAATA CTGCAGACCA
ATGTGCTAAT AGATGTACTA GGAATAATGG ACTTCCATTC ACTTGCAAGG
CCTTTGTTTT TGATAAAGCG AGAAAACAAT GCCTCTGGTT CCCCTTCAAT
AGCATGTCAA GTGGAGTGAA GAAAGAATTT GGCCATGAAT TTGACCTCTA
TGAAAACAAA GACTACATTA GAAACTGCAT CATCGGTAAA GGACGCAGCT
ACAAGGGAAC AGTATCTATC ACTAAGAGTG GCATCAAATG TCAGCCCTGG
AGTTCCATGA TACCACACGA ACACAGCTTT TTGCCTTCGA GCTATCGGGG
TAAAGACCTA CAGGAAAACT ACTGTCGAAA TCCTCGAGGG GAAGAAGGGG
GACCCTGGTG TTTCACAAGC AATCCAGAGG TACGCTACGA AGTCTGTGAC
ATTCCTCAGT GTTCAGAAGT TGAATGCATG ACCTGCAATG GGGAGAGTTA
TCGAGGTCTC ATGGATCATA CAGAATCAGG CAAGATTTGT CAGCGCTGGG
ATCATCAGAC ACCACACCGG CACAAATTCT TGCCTGAAAG ATATCCCGAC
AAGGGCTTTG ATGATAATTA TTGCCGCAAT CCCGATGGCC AGCCGAGGCC
ATGGTGCTAT ACTCTTGACC CTCACACCCG CTGGGAGTAC TGTGCAATTA
AAACATGCGC TGACAATACT GTAAATGATA CTGATGTTCC TATGGAAACA
ACTGAATGCA TCCAAGGTCA AGGAGAAGGC TACAGGGCA CTGCCAATAC
CATTTGGAAT GGAATTCCAT GTCAGCGTTG GGATTCTCAG TATCCTCACA
AGCATGACAT GACTCCTGAA AATTTCAAGT GCAAGGACCT ACGAGAAAAT
TACTGCCGAA ATCCAGATGG GTCTGAATCA CCCTGGTGTT TTACCACTGA
TCCAAACATC CGAGTTGGTT ACTGCTCCCA AATTCCAAAC TGTGATATGT
CAAATGGACA AGATTGTTAT CGTGGGAATG GCAAAAATTA TATGGGCAAC
TTATCCCAAA CAAGATCTGG ACTAACGTGT TCAATGTGGA ACAAGAACAT
GGAAGACTTA CACCGTCATA TCTTCTGGGA ACCAGATGCA AGTAAGCTGA
ATGAGAATTA CTGCCGAAAT CCAGATGATG ATGCTCATGG ACCCTGGTGC
TACACGGGAA ATCCACTCAT TCCTTGGGAT TATTGCCCTA TTTCTCGTTG
TGAAGGTGAT ACCACACCTA CAATAGTCCA GAGGCTCATG ATGCTCCTCG
CCACATCGGG CGCCTGCCTG GGCCTGCTGG CAGTGGCAGC AGTGGCAGCA
GCAGGTGCTA ACCCTGCCCA ACGGGACACC CACAGCCTGC TGCCCACCCA
CCGGCGCCAA AAGAGAGATT GGATTTGGAA CCAGATGCAC ATTGATGAAG
AGAAAAACAC CTCACTTCCC CATCATGTAG GCAAGATCAA GTCAAGCGTG
AGTCGCAAGA ATGCCAAGTA CCTGCTCAAA GGAGAATATG TGGGCAAGGT
CTTCCGGGTC GATGCAGAGA CAGGAGACGT GTTCGCCATT GAGAGGCTGG
ACCGGGAGAA TATCTCAGAG TACCACCTCA CTGCTGTCAT TGTGGACAAG
GACACTGGTG AAAACCTGGA GACTCCTTCC AGCTTCACCA TCAAA
```

Figure 2

```
KIDPALKIKTKKVNTADQCANRCTRNNGLPFTCKAFVFDKARKQ
CLWFPFNSMSSGVKKEFGHEFDLYENKDYIRNCIIGKGRSYKGT
VSITKSGIKCQPWSSMIPHEHSFLPSSYRGKDLQENYCRNPRGE
EGGPWCFTSNPEVRYEVCDIPQCSEVECMTCNGESYRGLMDHTE
SGKICQRWDHQTPHRHKFLPERYPDKGFDDNYCRNPDGQPRPWC
YTLDPHTRWEYCAIKTCADNTVNDTDVPMETTECIQGQGEGYRG
TANTIWNGIPCQRWDSQYPHKHDMTPENFKCKDLRENYCRNPDG
SESPWCFTTDPNIRVGYCSQIPNCDMSNGQDCYRGNGKNYMGNL
SQTRSGLTCSMWNKNMEDLHRHIFWEPDASKLNENYCRNPDDDA
HGPWCYTGNPLIPWDYCPISRCEGDTTPTIVQRLMMLLATSGAC
LGLLAVAAVAAAGANPAQRDTHSLLPTHRRQKRDWIWNQMHIDE
EKNTSLPHHVGKIKSSVSRKNAKYLLKGEYVGKVFRVDAETGDV
FAIERLDRENISEYHLTAVIVDKDTGENLETPSSFTIK
```

Figure 3

```
ATAGATCCAG CACTGAAGAT AAAAACCAAA AAAGTGAATA CTGCAGACCA
ATGTGCTAAT AGATGTACTA GGAATAATGG ACTTCCATTC ACTTGCAAGG
CCTTTGTTTT TGATAAAGCG AGAAAACAAT GCCTCTGGTT CCCCTTCAAT
AGCATGTCAA GTGGAGTGAA GAAAGAATTT GGCCATGAAT TTGACCTCTA
TGAAAACAAA GACTACATTA GAAACTGCAT CATCGGTAAA GGACGCAGCT
ACAAGGGAAC AGTATCTATC ACTAAGAGTG GCATCAAATG TCAGCCCTGG
AGTTCCATGA TACCACACGA ACACAGCTTT TTGCCTTCGA GCTATCGGGG
TAAAGACCTA CAGGAAAACT ACTGTCGAAA TCCTCGAGGG GAAGAAGGGG
GACCCTGGTG TTTCACAAGC AATCCAGAGG TACGCTACGA AGTCTGTGAC
ATTCCTCAGT GTTCAGAAGT TGAATGCATG ACCTGCAATG GGAGAGTTA
TCGAGGTCTC ATGGATCATA CAGAATCAGG CAAGATTTGT CAGCGCTGGG
ATCATCAGAC ACCACACCGG CACAAATTCT TGCCTGAAAG ATATCCCGAC
AAGGGCTTTG ATGATAATTA TTGCCGCAAT CCCGATGGCC AGCCGAGGCC
ATGGTGCTAT ACTCTTGACC CTCACACCCG CTGGGAGTAC TGTGCAATTA
AAACATGCGC TGACAATACT GTAAATGATA CTGATGTTCC TATGGAAACA
ACTGAATGCA TCCAAGGTCA AGGAGAAGGC TACAGGGGCA CTGCCAATAC
CATTTGGAAT GGAATTCCAT GTCAGCGTTG GGATTCTCAG TATCCTCACA
AGCATGACAT GACTCCTGAA AATTTCAAGT GCAAGGACCT ACGAGAAAAT
TACTGCCGAA ATCCAGATGG GTCTGAATCA CCCTGGTGTT TTACCACTGA
TCCAAACATC CGAGTTGGTT ACTGCTCCCA AATTCCAAAC TGTGATATGT
CAAATGGACA AGATTGTTAT CGTGGGAATG CAAAAATTA TATGGGCAAC
TTATCCCAAA CAAGATCTGG ACTAACGTGT TCAATGTGGA ACAAGAACAT
GGAAGACTTA CACCGTCATA TCTTCTGGGA ACCAGATGCA AGTAAGCTGA
ATGAGAATTA CTGCCGAAAT CCAGATGATG ATGCTCATGG ACCCTGGTGC
TACACGGGAA ATCCACTCAT TCCTTGGGAT TATTGCCCTA TTTCTCGTTG
TGAAGGTGAT ACCACACCTA CAATAGTC
```

Figure 4

```
                          AC CACACCTACA ATAGTCCACA
GAGGCTCATG ATGCTCCTCG CCACATCGGG CGCCTGCCTG
GGCCTGCTGG CAGTGGCAGC AGTGGCAGCA GCAGGTGCTA
ACCCTGCCCA ACGGGACACC CACAGCCTGC TGCCCACCCA
CCGGCGCCAA AAGAGAGATT GGATTTGGAA CCAGATGCAC
ATTGATGAAG AGAAAAACAC CTCACTTCCC CATCATGTAG
GCAAGATCAA GTCAAGCGTG AGTCGCAAGA ATGCCAAGTA
CCTGCTCAAA GGAGAATATG TGGGCAAGGT CTTCCGGGTC
GATGCAGAGA CAGGAGACGT GTTCGCCATT GAGAGGCTGG
ACCGGGAGAA TATCTCAGAG TACCACCTCA CTGCTGTCAT
TGTGGACAAG GACACTGGTG AAAACCTGGA GACTCCTTCC
AGCTTCACCA TCAAA
```

FIGURE 5

```
                                                   ACCATGATC
ATAGATCCAG CACTGAAGAT AAAAACCAAA AAAGTGAATA CTGCAGACCA
ATGTGCTAAT AGATGTACTA GGAATAATGG ACTTCCATTC ACTTGCAAGG
CCTTTGTTTT TGATAAAGCG AGAAAACAAT GCCTCTGGTT CCCCTTCAAT
AGCATGTCAA GTGGAGTGAA GAAAGAATTT GGCCATGAAT TTGACCTCTA
TGAAAACAAA GACTACATTA GAAACTGCAT CATCGGTAAA GGACGCAGCT
ACAAGGGAAC AGTATCTATC ACTAAGAGTG GCATCAAATG TCAGCCCTGG
AGTTCCATGA TACCACACGA ACACAGCTTT TTGCCTTCGA GCTATCGGGG
TAAAGACCTA CAGGAAAACT ACTGTCGAAA TCCTCGAGGG GAAGAAGGGG
GACCCTGGTG TTTCACAAGC AATCCAGAGG TACGCTACGA AGTCTGTGAC
ATTCCTCAGT GTTCAGAAGT TGAATGCATG ACCTGCAATG GGGAGAGTTA
TCGAGGTCTC ATGGATCATA CAGAATCAGG CAAGATTTGT CAGCGCTGGG
ATCATCAGAC ACCACACCGG CACAAATTCT TGCCTGAAAG ATATCCCGAC
AAGGGCTTTG ATGATAATTA TTGCCGCAAT CCCGATGGCC AGCCGAGGCC
ATGGTGCTAT ACTCTTGACC CTCACACCCG CTGGGAGTAC TGTGCAATTA
AAACATGCGC TGACAATACT GTAAATGATA CTGATGTTCC TATGGAAACA
ACTGAATGCA TCCAAGGTCA AGGAGAAGGC TACAGGGGCA CTGCCAATAC
CATTTGGAAT GGAATTCCAT GTCAGCGTTG GGATTCTCAG TATCCTCACA
AGCATGACAT GACTCCTGAA AATTTCAAGT GCAAGGACCT ACGAGAAAAT
TACTGCCGAA ATCCAGATGG GTCTGAATCA CCCTGGTGTT TTACCACTGA
TCCAAACATC CGAGTTGGTT ACTGCTCCCA AATTCCAAAC TGTGATATGT
CAAATGGACA AGATTGTTAT CGTGGGAATG GCAAAAATTA TATGGGCAAC
TTATCCCAAA CAAGATCTGG ACTAACGTGT TCAATGTGGA ACAAGAACAT
GGAAGACTTA CACCGTCATA TCTTCTGGGA ACCAGATGCA AGTAAGCTGA
ATGAGAATTA CTGCCGAAAT CCAGATGATG ATGCTCATGG ACCCTGGTGC
TACACGGGAA ATCCACTCAT TCCTTGGGAT TATTGCCCTA TTTCTCGTTG
TGAAGGTGAT ACCACACCTA CAATAGTC
```

FIGURE 6

GAGGCTCATG ATGCTCCTCG CCACATCGGG CGCCTGCCTG
GGCCTGCTGG CAGTGGCAGC AGTGGCAGCA GCAGGTGCTA
ACCCTGCCCA ACGGGACACC CACAGCCTGC TGCCCACCCA
CCGGCGCCAA AAGAGAGATT GGATTTGGAA CCAGATGCAC
ATTGATGAAG AGAAAAACAC CTCACTTCCC CATCATGTAG
GCAAGATCAA GTCAAGCGTG AGTCGCAAGA ATGCCAAGTA
CCTGCTCAAA GGAGAATATG TGGGCAAGGT CTTCCGGGTC
GATGCAGAGA CAGGAGACGT GTTCGCCATT GAGAGGCTGG
ACCGGGAGAA TATCTCAGAG TACCACCTCA CTGCTGTCAT
TGTGGACAAG GACACTGGTG AAAACCTGGA GACTCCTTCC
AGCTTCACCA TCAAA

FIGURE 7 ggcgcgcagtgcaccacctgcgtggccccgggcccggccaaggc gcgtgtggccctcacgggaggcgtgctctacctgttttgcgggc tgctggcgctcgtgccactctgctggttcgccaacattgtcgtc cgcgagttttacgaccgtctgtg

FIGURE 8 ggcgcgcagtgcaccacctgcgtggccccgggcccggccaaggcgcgtgtggccctcac
gggaggcgtgctctacctgttttgcgggctgctggcgctcgtgccactctgctggttcg
ccaacattgtcgtccgcgagttttacgaccgtctgtgccagcactgaagataaaaacc
aaaaaagtgaatactgcagaccaatgtgctaatagatgtactaggaataatggacttcc
attcacttgcaaggcctttgtttttgataaagcgagaaaacaatgcctctggttcccct
tcaatagcatgtcaagtggagtgaagaagaatttggccatgaatttgacctctatgaa
aacaaagactacattagaaactgcatcatcggtaaaggacgcagctacaagggaacagt
atctatcactaagagtggcatcaaatgtcagccctggagttccatgataccacacgaac
acagcttttgccttcgagctatcggggtaaagacctacaggaaaactactgtcgaaat
cctcgaggggaagaaggggggaccctggtgtttcacaagcaatccagaggtacgctacga
agtctgtgacattcctcagtgttcagaagttgaatgcatgacctgcaatggggagagtt
atcgaggtctcatggatcatacagaatcaggcaagatttgtcagcgctgggatcatcag
acaccacaccggcacaaattcttgcctgaaagatatcccgacaagggctttgatgataa
ttattgccgcaatcccgatggccagccgaggccatggtgctatactcttgaccctcaca
cccgctgggagtactgtgcaattaaaacatgcgctgacaatactgtaaatgatactgat
gttcctatggaaacaactgaatgcatccaaggtcaaggagaaggctacaggggcactgc
caataccatttggaatggaattccatgtcagcgttgggattctcagtatcctcacaagc
atgacatgactcctgaaaatttcaagtgcaaggacctacgagaaaattactgccgaaat
ccagatgggtctgaatcaccctggtgttttaccactgatccaaacatccgagttggtta
ctgctcccaaattccaaactgtgatatgtcaaatggacaagattgttatcgtgggaatg
gcaaaaattatatgggcaacttatcccaaacaagatctggactaacgtgttcaatgtgg
aacaagaacatggaagacttacaccgtcatatcttctgggaaccagatgcaagtaagct
gaatgagaattactgccgaaatccagatgatgatgctcatggaccctggtgctacacgg
gaaatccactcattccttgggattattgccctatttctcgttgtgaaggtgataccaca
cctacaatagtc

FIGURE 9 ggagtgaacccaactgctcagtcttctggatctctatatggttc
acaaatatatgccctctgcaccaatttta tacacctgcagcta
ctggactctacgtggatcagtatttgtatcactactgtgttgtg
gatccccaggag

FIGURE 10 ggagtgaacccaactgctcagtcttctggatctctatatggttcacaaatatatgccct
ctgcaaccaatttta tacacctgcagctactggactctacgtggatcagtatttgtatc
actactgtgttgtggatccccaggagccagcactgaagataaaaaccaaaaaagtgaat
actgcagaccaatgtgctaatagatgtactaggaataatggacttccattcacttgcaa
ggcctttgttttt gataaagcgagaaaacaatgcctctggttcccct tcaatagcatgt
caagtggagtgaagaaagaat ttggccatgaatttgacctctatgaaaacaaagactac
attagaaactgcatcatcggtaaaggacgcagctacaagggaacagtatctatcactaa
gagtggcatcaaatgtcagccctggagttccatgataccacgaacacagcttt ttgc
cttcgagctatcggggtaaagacctacaggaaaactactgtcgaaatcctcgaggggaa
gaaggggga ccctggtgtttcacaagcaatccagaggtacgctacgaagtctgtgacat
tcctcagtgttcagaagttgaatgcatgacctgcaatggggagagttatcgaggtctca
tggatcatacagaatcaggcaagatttgtcagcgctggatcatcagacaccacaccgg
cacaaattcttgcctgaaagatatcccgacaagggctttgatgataattattgccgcaa
tcccgatggccagccgaggccatggtgctatactcttgaccctcacaccgctgggagt
actgtgcaattaaaacatgcgctgacaatactgtaaatgatactgatgttcctatggaa
acaactgaatgcatccaaggtcaaggagaaggctacagggcactgccaataccatttg
gaatggaattccatgtcagcgttgggattctcagtatcctcacaagcatgacatgactc
ctgaaaatttcaagtgcaaggacctacgagaaaattactgccgaaatccagatgggtct
gaatcaccctggtgttttaccactgatccaaacatccgagttggttactgctcccaaat
tccaaactgtgatatgtcaaatggacaagattgttatcgtgggaatggcaaaaattata
tgggcaacttatcccaaacaagatctggactaacgtgttcaatgtggaacaagaacatg
gaagacttacaccgtcatatcttctgggaaccagatgcaagtaagctgaatgagaatta
ctgccgaaatccagatgatgatgctcatggaccctggtgctacacgggaaatccactca
ttccttgggattattgccctatttctcgttgtgaaggtgataccacacctacaatagtc

FIGURE 11 accatgggagtgaacccaactgctcagtcttctggatctctata
tggttcacaaatatatgccctctgcaaccaattttatacacctg
cagctactggactctacgtggatcagtatttgtatcactactgt
gttgtggatccccaggag

FIGURE 12 accatgggagtgaacccaactgctcagtcttctggatctctatatggttcacaaatata
tgccctctgcaaccaattttatacacctgcagctactggactctacgtggatcagtatt
tgtatcactactgtgttgtggatccccaggaggattggatttggaaccagatgcacatt
gatgaagagaaaaacacctcacttccccatcatgtaggcaagatcaagtcaagcgtgag
tcgcaagaatgccaagtacctgctcaaggagaatatgtgggcaaggtcttccgggtcg
atgcagagacaggagacgtgttcgccattgagaggctggaccgggagaatatctcagag
taccacctcactgctgtcattgtggacaaggacactggtgaaaacctggagactccttc
cagcttcaccatcaaagttcatgacgtgaacgacaactggcctgtgttcacgcatcggt
tgttcaatgcgtccgtgcctgagtcgtcggctgtggggacctcagtcatctctgtgaca
gcagtggatgcagacgaccccactgtgggagaccacgcctctgtcatgtaccaaatcct
gaaggggaaagagtattttgccatcgataattctggacgtattatcacaataacgaaaa
gcttggaccgagagaagcaggccaggtatgagatcgtggtggaagcgcgagatgcccag
ggcctccgggggggactcgggcacggccaccgtgctggtcactctgcaagacatcaatga
caacttccccttcttcacccagaccaagtacacatttgtcgtgcctgaagacacccgtg
tgggcacctctgtgggctctctgtttgttgaggacccagatgagccccagaaccggatg
accaagtacagcatcttgcggggcgactaccaggacgctttcaccattgagacaaaccc
cgcccacaacgagggcatcatcaagcccatgaagcctctggattatgaatacatccagc
aatacagcttcatcgtcgaggccacagaccccaccatcgacctccgatacatgagccct
cccgcgggaaacagagcccaggtcatta1200tcaacatcacagatgtggacgagcccc
ccattttccagcagccttctctaccacttccagctgaaggaaaaccagaagaagcctctg
attggcacagtgctggccatggaccctgatgcggctaggcatagcattggatactccat
ccgcaggaccagtgacaagggccagttcttccgagtcacaaaaaaggggggacatttaca
atgagaaagaactggacagagaagtctaccctggtataacctgactgtggaggccaaa
gaactggattccactggaaccccacaggaaaagaatccattgtgcaagtccacattga
agtttggatgagaatgacaatgccccggagtttgccaagccctaccagcccaaagtgt
gtgagaacgctgtccatggccagctggtcctgcagatctccgcaatagacaaggacata
acaccacgaaacgtgaagttcaaattcatcttgaatactgagaacaactttaccctcac
ggataatcacgataacacggccaacatcacagtcaagtatgggcagtttgaccgggagc
ataccaaggtccacttcctacccgtggtcatctcagacaatgggatgccaagtcgcacg
ggcaccagcacgctgaccgtggccgtgtgcaagtgcaacgagcagggcgagttcacctt
ctgcgaggatatggccgcccag

FIGURE 13

GAQCTTCVAPGPAKARVALTGGVLYLFCGLLALVPLCWFANIVVREFYDP
SVPVSKIDPALKIKTKKVNTADQCANRCTRNNGLPFTCKAFVFDKARKQC
LWFPFNSMSSGVKKEFGHEFDLYENKDYIRNCIIGKGRSYKGTVSITKSG
IKCQPWSSMIPHEHSFLPSSYRGKDLQENYCRNPRGEEGGPWCFTSNPEV
RYEVCDIPQCSEVECMTCNGESYRGLMDHTESGKICQRWDHQTPHRHKFL
PERYPDKGFDDNYCRNPDGQPRPWCYTLDPHTRWEYCAIKTCADNTVNDT
DVPMETTECIQGQGEGYRGTANTIWNGIPCQRWDSQYPHKHDMTPENFKC
KDLRENYCRNPDGSESPWCFTTDPNIRVGYCSQIPNCDMSNGQDCYRGNG
KNYMGNLSQTRSGLTCSMWNKNMEDLHRHIFWEPDASKLNENYCRNPDDD
AHGPWCYTGNPLIPWDYCPISRCEGDTTPTIV

FIGURE 14

GVNPTAQSSGSLYGSQIYALCNQFYTPAATGLYVDQYLYHYCVVDPQEKI
DPALKIKTKKVNTADQCANRCTRNNGLPFTCKAFVFDKARKQCLWFPFNS
MSSGVKKEFGHEFDLYENKDYIRNCIIGKGRSYKGTVSITKSGIKCQPWS
SMIPHEHSFLPSSYRGKDLQENYCRNPRGEEGGPWCFTSNPEVRYEVCDI
PQCSEVECMTCNGESYRGLMDHTESGKICQRWDHQTPHRHKFLPERYPDK
GFDDNYCRNPDGQPRPWCYTLDPHTRWEYCAIKTCADNTVNDTDVPMETT
ECIQGQGEGYRGTANTIWNGIPCQRWDSQYPHKHDMTPENFKCKDLRENY
CRNPDGSESPWCFTTDPNIRVGYCSQIPNCDMSNGQDCYRGNGKNYMGNL
SQTRSGLTCSMWNKNMEDLHRHIFWEPDASKLNENYCRNPDDDAHGPWCY
TGNPLIPWDYCPISRCEGDTTPTIV

FIGURE 15

GVNPTAQSSGSLYGSQIYALCNQFYTPAATGLYVDQYLYHYCVVDPQEDW
IWNQMHIDEEKNTSLPHHVGKIKSSVSRKNAKYLLKGEYVGKVFRVDAET
GDVFAIERLDRENISEYHLTAVIVDKDTGENLETPSSFTIKVHDVNDNWP
VFTHRLFNASVPESSAVGTSVISVTAVDADDPTVGDHASVMYQILKGKEY
FAIDNSGRIITITKSLDREKQARYEIVVEARDAQGLRGDSGTATVLVTLQ
DINDNFPFFTQTKYTFVVPEDTRVGTSVGSLFVEDPDEPQNRMTKYSILR
GDYQDAFTIETNPAHNEGIIKPMKPLDYEYIQQYSFIVEATDPTIDLRYM
SPPAGNRAQVIINITDVDEPPIFQQPFYHFQLKENQKKPLIGTVLAMDPD
AARHSIGYSIRRTSDKGQFFRVTKKGDIYNEKELDREVYPWYNLTVEAKE
LDSTGTPTGKESIVQVHIEVLDENDNAPEFAKPYQPKVCENAVHGQLVLQ
ISAIDKDITPRNVKFKFTLNTENNFTLTDNHDNTANITVKYGQFDREHTK
VHFLPVVISDNGMPSRTGTSTLTVAVCKCNEQGEFTFCEDMAAQ

FIGURE 16

```
ccagcactgaagataaaaccaaaaaagtgaatactgcagacca
atgtgctaatagatgtactaggaataatggacttccattcactt
gcaaggcctttgttttgataaagcgagaaaacaatgcctctgg
ttcccttcaatagcatgtcaagtggagtgaagaaagaatttgg
ccatgaatttgacctctatgaaacaaagactacattagaaact
gcatcatcggtaaaggacgcagctacaagggaacagtatctatc
actaagagtggcatcaaatgtcagccctggagttccatgatacc
acacgaacacagcttttgcttcgagctatcggggtaaagacc
tacaggaaaactactgtcgaatcctcgaggggaagaagggga
ccctggtgtttcacaagcaatccagaggtacgctacgaagtctg
tgacattcctcagtgttcagaagttaatgcatgacctgcaatg
gggagagttatcgaggtctcatggatcatacagaatcaggcaag
atttgtcagcgctgggatcatcagacaccacaccggcacaaatt
cttgcctgaaagatatcccgacaagggctttgatgataattatt
gccgcaatcccgatggccagccgaggccatggtgctatactctt
gaccctcacaccgctgggagtactgtgcaattaaaacatgcgc
tgacaatactgtaaatgatactgatgttcctatggaaacaactg
aatgcatccaaggtcaaggagaaggctacaggggcactgccaat
accatttggaatggaattccatgtcagcgttgggattctcagta
tcctcacaagcatgacatgactcctgaaaatttcaagtgcaagg
acctacgagaaattactgccgaaatccagatgggtctgaatca
ccctggtgtttaccactgatccaaacatccgagttggttactg
ctcccaaattccaactgtgatatgtcaaatggacaagattgtt
atcgtgggaatggcaaaaattatgggcaacttatcccaaaca
agatctggactaacgtgttcaatgtggaacaagaacatggaaga
cttacaccgtcatatcttctgggaaccagatgcaagtaagctga
atgagaattactgccgaaatccagatgatgatgctcatggaccc
tggtgctacacgggaaatccactcattccttgggattattgccc
tatttctcgttgtgaaggtgataccacactacaatagtc
```

FIGURE 17 ccagcactgaagataaaaaccaaaaaagtgaatactgcagacca
atgtgctaatagatgtactaggaataatggacttccattcactt
gcaaggcctttgttttgataaagcgagaaacaatgcctctgg
ttcccttcaatagcatgtcaagtggagtgaagaaagaatttgg
ccatgaatttgacctctatgaaacaagactacattagaact
gcatcatcggtaaggacgcagctacaagggaacagtatctatc
actaagagtggcatcaaatgtcagcctggagttccatgatacc
acacgaacacagcttttgccttcgagctatcggggtaaagacc
tacaggaaaactactgtcgaatcctcgaggggaagaaggggga
ccctggtgtttcacaagcaatccagaggtacgctacgaagtctg
tgacattcctcagtgttcagaagttgaatgcatgacctgcaatg
gggagagttatcgaggtctcatggatcatacagaatcaggcaag
atttgtcagcgctggatcatcagacaccacaccggcacaaatt
cttgcctgaaagatatcccgacaagggctttgatgataattatt
gccgcaatccgatggccagccgaggccatggtgctatactctt
gaccctcacacccgctgggagtactgtgcaattaaaacatgcgc
tgacaatactgtaaatgatactgatgttcctatggaaacaactg
aatgcatccaaggtcaaggagaaggctacaggggcactgccaat
accatttggaatggaattccatgtcagcgttgggattctcagta
tcctcacaagcatgacatgactcctgaaatttcaagtgcaagg
acctacgagaaattactgccgaaatccagatgggtctgaatca
ccctggtgttttaccactgatccaaacatccgagttggttactg
ctcccaaattccaactgtgatatgtcaaatggacaagattgtt
atcgtgggaatggcaaaattatatgggcaacttatcccaaaca
agatctggactaacgtgttcaatgtggaacaagaacatggaaga
cttacaccgtcatatcttctgggaaccagatgcaagtaagctga
atgagaattactgccgaaatccagatgatgatgctcatggaccc
tggtgctacacgggaaatccactcattccttgggattattgccc
tatttctcgttgtgaaggtgataccacctacaatagtc

FIGURE 18

```
gattggatttggaaccagatgcacattgatgaagagaaaaacacctcact
tccccatcatgtaggcaagatcaagtcaagcgtgagtcgcaagaatgcca
agtacctgctcaaaggagaatatgtgggcaaggtcttccgggtcgatgca
gagacaggagacgtgttcgccattgagaggctggaccgggagaatatctc
agagtaccacctcactgctgtcattgtggacaaggacactggtgaaaacc
tggagactccttccagcttcaccatcaaagttcatgacgtgaacgacaac
tggcctgtgttcacgcatcggttgttcaatgcgtccgtgcctgagtcgtc
ggctgtggggacctcagtcatctctgtgacagcagtggatgcagacgacc
ccactgtgggagaccacgcctctgtcatgtaccaaatcctgaaggggaaa
gagtattttgccatcgataattctggacgtattatcacaataacgaaaag
cttggaccgagagaagcaggccaggtatgagatcgtggtggaagcgcgag
atgcccagggcctccggggggactcggcacggccaccgtgctggtcact
ctgcaagacatcaatgacaacttccccttcttcacccagaccaagtacac
atttgtcgtgcctgaagacacccgtgtgggcacctctgtgggctctctgt
ttgttgaggacccagatgagccccagaaccggatgaccaagtacagcatc
ttgcggggcgactaccaggacgctttcaccattgagacaaacccgccca
caacgagggcatcatcaagcccatgaagcctctggattatgaatacatcc
agcaatacagcttcatcgtcgaggccacagacccaccatcgacctcga
tacatgagccctcccgcgggaaacagagcccaggtcatta1200tcaaca
tcacagatgtggacgagccccccatttccagcagcctttctaccacttc
cagctgaaggaaaaccagaagaagcctctgattggcacagtgctggccat
ggaccctgatgcggctaggcatagcattggatactccatccgcaggacca
gtgacaagggccagttcttccgagtcacaaaaaaggggggacatttacaat
gagaaagaactggacagagaagtctacccctggtataacctgactgtgga
ggccaaagaactggattccactggaaccccacaggaaaagaatccattg
tgcaagtccacattgaagttttggatgagaatgacaatgccccggagttt
gccaagccctaccagcccaaagtgtgtgagaacgctgtccatggccagct
ggtcctgcagatctccgcaatagacaaggacataacaccacgaaacgtga
agttcaaattcatcttgaatactgagaacaactttaccctcacggataat
cacgataacacggccaacatcacagtcaagtatgggcagtttgaccggga
gcataccaaggtccacttcctacccgtggtcatctcagacaatgggatgc
caagtcgcacgggcaccagcacgctgaccgtggccgtgtgcaagtgcaac
gagcagggcgagttcaccttctgcgaggatatggccgcccag
```

RECOMBINANT SEQUENCE, ITS PREPARATION AND USE

The present invention relates to a recombinant nucleic acid sequence encoding both a specific angiogenesis factor antagonist and a vascular endothelial structure regulator; its preparation; protein expression; and the use of the sequence or the protein in the inhibition of angiogenesis and/or the treatment of cancer.

Angiogenesis, the formation of new blood vessels, is a key in the development and progression of cancer. Angiogenesis is governed by a range of angiogenic factors and anti-angiogenic factors. Angiogenic factors are known to include a range of cytokines, such as vascular endothelial growth factor (VEGF), fibroblast growth factor (FGF) eg Basic FGF (bFGF), interleukins (ILs, eg IL-8) and hepatocyte growth factor/scatter factor (HGF/SF). Without new blood vessels, a tumour can not grow beyond 2 mm in diameter, due to limited blood supply and nutrient/oxygen diffusion.

Furthermore, tumour cells may disseminate in the body and produce micro- and macro-metastasis in organs and tissues, but remain invisible for from months to years. Once new blood vessels grow into these quiescent tumours, they will grow at a much faster speed, begin to manifest clinical symptoms and become lethal to patients. New blood vessels in the tumour provide not only nutrients and oxygen, but also a passage for tumour cells to enter the circulation and therefore aid the process of metastasis.

Therefore, anti-angiogenesis has become a focus in the development of new anti-cancer drugs. The fundamental importance of angiogenesis in cancer development and metastasis has prompted the discovery of a large number of angiogenesis inhibitors, including agents specifically designed as anti-angiogenesis agents (such as anti-VEGF antibody, anti-bFGF antibody, fumagillin and recombinant products based on a single gene, such as angiostatin), and those discovered unintentionally (such as beta-inteferon, tamoxifen and interleukins-4 and -12).

Some of the angiogenic factor antagonists are suitable for the purpose of anti-angiogenesis, but others are not. For example, each antagonist works specifically on only one particular angiogenic factor, whereas there are about 20–40 angiogenic factors in the body, in any given tumour. Another problem is that using a specific antagonist will result in a balance switch in which the targeted angiogenic factor is suppressed, but other factor(s) increase in compensation. Hence, the balance shifts from the targeted angiogenic factor to another or others, resulting in resistance to anti-angiogenesis therapy.

Accordingly, the present invention is directed to an agent to suppress angiogenesis, obtainable by genetically engineering two important regulators of angiogenesis, an angiogenic factor antagonist and an endothelial structure regulator (such as vascular endothelial cadherin).

We have therefore genetically engineered a recombinant molecule that comprises both a sequence capable of expressing a specific antagonist and a sequence capable of expressing a specific endothelial cell marker, being a vascular endothelial structure regulator, which is essential to the formation of new blood vessels. The recombinant products (referred to collectively herein as KV products, such as those referred to as KVEn, wherein n is an integer, K represents the angiogenic factor antagonist, V represents vascular endothelial cells and E represents the expression vector, and others referred to by J numbers) both retain the antagonistic properties of an anti-angiogenic factor; and also specifically recognise cells that produce new blood vessels, ie vascular endothelial cells.

Therefore, the recombinant products will work on the general mechanism for forming new blood vessels as well as on a specific mechanism operated by a specific angiogenic factor; and have the further advantage in preventing the balance switch and angiogenesis resistance that currently faces anti-angiogenesis therapy.

Accordingly, the present invention provides an isolated, purified or recombinant nucleic acid sequence (hereinafter, a KV sequence) comprising:
(a) a sequence that encodes both an angiogenic factor antagonist and a vascular endothelial structure regulator;
(b) a sequence substantially homologous to or that hybridises to sequence (a) under stringent conditions; or
(c) a sequence substantially homologous to or that hybridises under stringent conditions to the sequence (a) or (b) but for the degeneracy of the genetic code; or
(d) an oligonucleotide specific for any of the sequences (a), (b) or (c).

By 'homologous' herein is meant a sequence having at least 80% identity of nucleotides (or, in the case of an amino acid sequence, bases) in the same order within the sequence. Preferably, the sequence has at least 85% and more preferably at least 90%, such as over 95% homology.

The present invention further provides a polypeptide (protein) sequence (of amino acids) encoded by a nucleotide sequence of the invention.

Specific embodiments of the present invention will therefore now be described with reference to the accompanying Figures, in which:

FIG. 1 is the nucleic acid sequence (SEQ ID NO: 1) of the recombinant KVE702, having 1695 nucleic acids;

FIG. 2 is the predicted amino acid sequence (SEQ ID NO: 2) of KVE702 protein, encoded by the recombinant KVE702 sequence, reading from position 1 and having 566 amino acids;

FIG. 3 is that part of the sequence (SEQ ID NO: 3) of FIG. 1 derived from MRC-5 (the angiogenic antagonist component, KS2101);

FIG. 4 is that part of the sequence (SEQ ID NO: 4) of FIG. 1 derived from HUVEC (the vascular endothelial structure regulator component, VC503);

FIG. 5 is the nucleic acid sequence (SEQ ID NO: 5) of KS2105;

FIG. 6 is the nucleic acid sequence (SEQ ID NO: 6) of VC1;

FIG. 7 is the nucleic acid sequence (SEQ ID NO: 7) of J12;

FIG. 8 is the nucleic acid sequence (SEQ ID NO: 8) of the recombinant J35;

FIG. 9 is the nucleic acid sequence (SEQ ID NO: 9) of J11;

FIG. 10 is the nucleic acid sequence (SEQ ID NO: 10) of the recombinant J36;

FIG. 11 is the nucleic acid sequence (SEQ ID NO: 11) of J8;

FIG. 12 is the nucleic acid sequence (SEQ ID NO: 12) of J37;

FIG. 13 is the predicted amino acid sequence (SEQ ID NO: 13) for J35 protein, corresponding to the nucleic acid sequence (SEQ ID NO: 8) of FIG. 8;

FIG. 14 is the predicted amino acid sequence (SEQ ID NO: 14) for J36 protein, corresponding to the nucleic acid sequence (SEQ ID NO: 10) of FIG. 10;

FIG. 15 is the predicted amino acid sequence (SEQ ID NO: 15) for J37 protein, corresponding to the nucleic acid sequence (SEQ ID NO: 12) of FIG. 12;

FIG. 16 is the nucleic acid sequence (SEQ ID NO: 16) of J9;

FIG. 17 is the nucleic acid sequence (SEQ ID NO: 17) of J10; and

FIG. 18 is the nucleic acid sequence (SEQ ID NO: 18) of J6.

Particular oligonucleotides (d) that are included in this invention are those encoding the vascular endothelial structure regulator. The endothelial structure regulator is suitably derived from VE-cadherin, E-selectin, occludin, claudin-5 and/or vascular cell adhesion molecule (VCAM), especially VE-cadherin, occluding and claudin-5.

Accordingly, the present invention further provides an isolated, purified or recombinant nucleic acid sequence (hereinafter, a KV sequence) comprising:
(a) a sequence that encodes a vascular endothelial structure regulator, such as VC1, VC503, J8, J11 and J12, as defined below;
(b) a sequence substantially homologous to or that hybridises to sequence (a) under stringent conditions; or
(c) a sequence substantially homologous to or that hybridises under stringent conditions to the sequence (a) or (b) but for the degeneracy of the genetic code; or
(e) an oligonucleotide specific for any of the sequences (a), (b) or (c).

The antagonist fragment is suitably derived from VEGF, bFGF, hepatocyte growth factor/scatter factor (HGF/SF) and/or chemokines. Preferably, the antagonist fragment is derived from VEGF and/or HGF/SF. Particularly preferred antagonist fragments are KS2101 and KS2105, as defined below.

In general, such products may be prepared by using a conventional recombinant DNA technique. For example, first, a plurality of separate DNA fragments are prepared, at least one of which comprises a sequence encoding an antagonist and at least one of which comprises a sequence encoding the endothelial structure regulator. This may be carried out with specific primers that allow a further recombinant to be prepared, which generates a new recombinant gene. In particular, certain recombinant genes, referred to hereinbelow as KVE702, J35, J36 and J37, have been generated from DNA fragments cloned from human fibroblasts and vascular endothelial cells. The new KVE702 gene and its fragments have been used to transfect human epithelial cells and to generate products that may be suitable for angiogenesis intervention.

Accordingly, the present invention further provides an isolated, purified or recombinant nucleic acid sequence comprising:
(a) a sequence that encodes both an angiogenic factor antagonist derivable from a human fibroblast cell line, preferably MRC-5, and a vascular endothelial structure regulator comprised in human vascular endothelial cells (HUVEC) extractable from human umbilical vein;
(b) a sequence substantially homologous to or that hybridises to sequence (a) under stringent conditions; or
(c) a sequence substantially homologous to or that hybridises under stringent conditions to the sequence (a) or (b) but for the degeneracy of the genetic code; or
(d) an oligonucleotide specific for any of the sequences (a), (b) or (c).

The MRC-5 cell line is available from the European Collection of Animal Cell Cultures, and HUVEC is obtainable by extraction from fresh umbilical cord.

Preferably, the sequence (a) is selected from the following:
as shown in FIG. 1, [SEQ ID NO: 1] [KVE702 sequence];
as shown in FIG. 8, [SEQ ID NO: 8] [J35 sequence];
as shown in FIG. 10, [SEQ ID NO: 10] [J36 sequence]; and,
as shown in FIG. 12, [SEQ ID NO: 12] [J37 sequence];

That part of the sequence according to the invention [KVE702 sequence] derived from the MRC-5 cell line is shown in FIG. 3 [SEQ ID NO 3], being a first part (the KS2101 component) of the KVE702 sequence. That part of the sequence according to the invention [KVE702 sequence] derived from HUVEC is shown in FIG. 4 [SEQ ID NO 4], being the remaining part (the VC503 component) of the KVE702 sequence.

That part of the sequence according to the invention [J35 sequence] derived from the MRC-5 cell line is shown in FIG. 16 [SEQ ID NO16], being a first part (the J9 component) of the J35 sequence. That part of the sequence according to the invention [J35 sequence] derived from HUVEC is shown in FIG. 7 [SEQ ID NO 7], being the remaining part (the J12 component) of the J35 sequence.

That part of the sequence according to the invention [J36 sequence] derived from the MRC-5 cell line is shown in FIG. 17 [SEQ ID NO17], being a first part (the J10 component) of the J36 sequence. That part of the sequence according to the invention [J36 sequence] derived from HUVEC is shown in FIG. 9 [SEQ ID NO 9], being the remaining part (the J11 component) of the J36 sequence.

That part of the sequence according to the invention [J37 sequence] derived from the MRC-5 cell line is shown in FIG. 18 [SEQ ID NO 18], being a first part (the J6 component) of the J37 sequence. That part of the sequence according to the invention [J37 sequence] derived from HUVEC is shown in FIG. 11 [SEQ ID NO 11], being the remaining part (the J8 component) of the J37 sequence.

Using these cloned products, it is possible to transfect a suitable cell and establish stable transfectants to see whether the transfection affects the motile behaviour of the transfected cells. Determination of a suitable cell for transfection is carried out by usual trial-and-error methods known in the art in which, for example, human epithelial, fibroblast or leukaemic cells are transfected with a plasmid carrying both the gene and an antibiotic resistance gene, to which toxic antibiotics (such as G418, available from InVitrogen) are added. Cells that are able to incorporate the gene will therefore die as a result of the antibiotic, thereby allowing exclusion of cells unsuitable for transfection. An example of such suitable cells is the human breast cancer cell line, MCF-7. The transfectants can then be used to generate recombinant proteins for testing in an angiogenesis assay and subsequent selection for therapeutic and/or diagnostic use.

Accordingly, the present invention further provides an isolated, purified or recombinant construct incorporating a KV sequence according to the above description, in particular, one wherein the nucleic acid sequence is linked operably with nucleotides enabling expression and secretion in a cellular host of a protein (hereinafter, the KV protein) encoded by the KV sequence.

Furthermore, this invention provides DNA or RNA, especially cDNA or mRNA, according to any of the aforementioned sequences or constructs; and a method for preparing such DNA or RNA as described herein, together with such DNA or RNA preparable by such a method.

Accordingly, the present invention also provides a method for preparing a KV sequence, which method comprises:

(a) generating a fragment of cDNA encoding a specific angiogenesis factor antagonist;
(b) generating a fragment of cDNA encoding a specific vascular endothelial structure regulator, which fragments (a) and (b) are complementary at one end thereof; and
(c) combining the fragments to generate a recombinant gene capable of expressing the corresponding KV protein.

Especially, the present invention provides an isolated, purified or recombinant polypeptide comprising both an angiogenic factor antagonist and a vascular endothelial structure regulator, such as those mentioned herein; and, in particular, an isolated, purified or recombinant polypeptide comprising KV protein, or a mutant or variant thereof having substantially the same activity as KV protein.

For example, there is provided an isolated, purified or recombinant polypeptide comprising an amino acid sequence selected from FIG. 2, [SEQ ID NO: 2][predicted KVE702 protein]; FIG. 13, [SEQ ID NO: 13] [predicted J35 protein]; FIG. 14, [SEQ ID NO: 14] [predicted J36 protein]; and FIG. 15, [SEQ ID NO: 15] [predicted J37 protein]; or any KV protein when expressed by a DNA sequence according to this invention.

It will be apparent that the invention therefore further provides a cell, plasmid, virus or live organism that has been genetically-engineered to produce a KV protein, said cell, plasmid, virus or live organism having incorporated expressibly therein a KV nucleotide sequence according to this invention; a vector comprising such a sequence; and/or a host cell transformed or transfected with such a vector.

For gene therapy, preferably a viral vector would be chosen and genetically-engineered to produce the KV protein. Both retroviral and adenoviral vectors could be used, such as the Retro-X™ or Adeno-X™ systems from Clontech (USA).

Furthermore, this invention provides a process for obtaining a substantially homologous source of KV protein, which process comprises culturing cells having incorporated expressibly therein a KV nucleotide sequence according to this invention, and thereafter recovering the cultured cells.

The KV protein(s) according to this invention may therefore be used in connection with any condition associated with angiogenesis, such as cancer, for the regulation of the development of blood vessels and their formation, whether in the vascular endothelium and/or a tumour. A suitable dose may be determined according to conventional techniques known to those skilled in the art of pharmacy, but may conveniently be in the range of from 0.5 to 10 mg/kg bodyweight, administered in a suitable regime, such as from once to seven times per week.

Accordingly, the present invention still further provides such a KV protein, optionally in association with a pharmaceutically acceptable carrier therefor, for use in therapy, such as for use in any of the conditions mentioned herein. It is especially preferred that, for protein therapy, there is provided a pharmaceutical formulation comprising such a protein (KV protein) in association with a pharmaceutically acceptable carrier therefor. Preferred formulations include those for parenteral administration, such as injections and infusions for intravenous or intramuscular administration. Other suitable formulations are well-known to those skilled in the art of pharmaceuticals.

Also provided are:

a method for preparing such formulations, which method comprises bringing the protein (KV protein) into association with the carrier;

a method for the prophylaxis or treatment of a mammal, including man, comprising the administration to said mammal of a non-toxic, effective amount of such a protein (KV protein);

a KV protein for use in medicine, such as in the inhibition of angiogenesis and/or the treatment of cancer; and the use of a KV protein in the preparation of a medicament, suitable for use in the inhibition of angiogenesis and/or the treatment of cancer.

The following examples are provided by way of illustration of the present invention.

EXAMPLE 1

Cloning of KVE702 Recombinant Gene

Cells Used

Human fibroblasts (an established cell line, MRC-5) and human vascular endothelial cells (HUVEC) (extracted from human umbilical vein) (Cai J et al. Gamma linolenic acid inhibits expression of VE-cadherin and tube formation in human vascular endothelial cells. Biochemical and Biophysical Research Communications, 1999, 258, 113–118) were used.

Preparation of Human mRNA and cDNA Template mRNA was isolated from fibroblasts or endothelial cells using an mRNA extraction kit (Sigma Chemicals, Poole, Dorset, UK). Complementary DNA (cDNA) was prepared from the mRNA using a reverse transcription kit (Promega).

Oligonucleotides (Primers) Used in PCR Reaction and Recombinant PCR

Sets of PCR primers were designed to amplify the areas of interest from the prepared cDNA, ie antagonist from the fibroblasts and endothelial marker/antagonist from the endothelial cells. The PCR primers were designed in such way that the products of each reaction would be used in the subsequent recombination. The primers were synthesised by Life Technologies and used exclusively for this work. Those primers designed for the cloning of the recombinant gene named herein KVE702 were as follows:

| | | |
|---|---|---|
| i | CAT GAG CCT CTG GAC TAT TGT AGG TGT GGT | (SEQ ID NO: 19) |
| ii | ACC ACA CCT ACA ATA GTC CAG AGG CTC ATG AT | (SEQ ID NO: 20) |
| iii | ACC ATG GAT CCA GCA CTG AAG ATA AAA ACC | (SEQ ID NO: 21) |
| iv | TTT GAT GGT GAA GCT GGA | (SEQ ID NO: 22) |

The amplification was carried out at three separate settings: first, to generate a fragment from fibroblast cDNA and, secondly, to generate a fragment from HUVEC cDNA, both products being complementary at one end. The final step was to generate a recombinant product by joining the two fragments. Each reaction was performed under special conditions in order to generate the desired products, as follows:

Setting 1 (to generate antagonist): 95° C. for 5 minutes, then 36 cycles of 95° C. for 1 minute, 61° C. for 1 minute and 72° C. for 2 minutes, followed by 72° C. for 7 minutes.

Setting 2 (to generate endothelial marker): 95° C. for 5 minutes, then 36 cycles of 95° C. for 40 seconds, 58° C. for 2 minutes and 72° C. for 2 minutes, followed by 72° C. for 10 minutes.

Setting 3 (to generate recombinant gene): without primer at 95° C. for 5 minutes, then 4 cycles of 95° C. for 40 seconds, 35° C. for 1 minute and 72° C. for 90 seconds, followed by 72° C. for 90 seconds, then 4 cycles of 95° C. for 40 seconds, 40° C. for 1 minute and 72° C. for 90 seconds, followed by 72° C. for 90 seconds, then 4 cycles of 95° C. for 40 seconds, 45° C. for 1 minute and 72° C. for 90 seconds, followed by 72° C. for 90 seconds, then 4 cycles of 95° C. for 40 seconds, 50° C. for 1 minute and 72° C. for 90 seconds, followed by 72° C. for 90 seconds, then 4 cycles of 95° C. for 40 seconds, 55° C. for 1 minute and 72° C. for 90 seconds, followed by 72° C. for 90 seconds, then 4 cycles of 95° C. for 40 seconds, 60° C. for 1 minute and 72° C. for 90 seconds, followed by 72° C. for 90 seconds, then 4 cycles of 95° C. for 40 seconds, 64° C. for 1 minute and 72° C. for 90 seconds, followed by 72° C. for 90 seconds, followed by 72° C. for 10 minutes;

then, with primers added, 35 cycles of 95° C. for 40 seconds, 59° C. for 1 minute and 72° C. for 90 seconds, followed by 72° C. for 10 minutes.

From these reactions, the following products were generated:

1. DNA fragments were isolated from fibroblasts using RT-PCR, referred to herein as: KS2101 (FIG. 3, [SEQ ID NO: 3]) & KS2105 (FIG. 5, [SEQ ID NO: 5]) (relating to the antagonist). KS2105 is related to KS2101, but not having a tail corresponding to the endothelial marker. KS2105 was prepared by using the following additional primer:

v GAC TAT TGT AGG TGT (SEQ ID NO: 23)
  GGT ATC

2. DNA fragments from HUVEC cells, referred to herein as: VC503 (FIG. 4, [SEQ ID NO: 4]) and VC1 (FIG. 6, [SEQ ID NO: 6]) (both relating to vascular endothelial structure regulators). VC1 is related to VC503 by not having a tail corresponding to the antagonist and was prepared by using the following additional primer:

v GTG TCC TTG TCC ACA (SEQ ID NO: 24)
  ATG ACT

3. The recombinant sequence: A further step was carried out to generate the recombinant sequence, by joining KS2101 and VC503, using the aforementioned recombinant technique. This generated a specific recombinant sequence, namely KVE702 (FIG. 1, [SEQ ID NO: 1]).

Cloning of the Specific Products

Each fragment and the recombinant gene were cloned into a mammalian expression vector (pcDNA3.1/V5/His-TOPO, available from InVitrogen) and transfected into a competent E. coli. Colonies that carried the desired products were detected using PCR. The positive colonies were further expanded and grown in large volume. Plasmids resulting from cloning the genes into the vector (ie that carried the specific products) were then purified from these E. coli preparations.

EXAMPLE 2

Transfection and Establishment of a KVE702-Expressing Cell

KS2101, KS2105, VC1, VC503 and KVE702 gene-carrying plasmids were transfected into mammalian epithelial cells. A transfection agent, Transfast (Promega), was used. After series testing, MCF-7 cells (well-known as a human breast cancer cell line) were found to be the most suitable and acceptable cell for this purpose and chosen to be the cells for transfection in the current study. The optimal transfection condition was at Transfast:DNA=2:1.

After transfection, cells that retained these new genes were selected using a selection medium containing G418 (from InVitrogen or Calbiochem), which caused cells that had no new genes gradually to die out whilst those with new genes carried on dividing. Cells expressing these new genes of interest were obtained after over 4 weeks' selection (so-called stable transfectants). It was observed that wild type (non-transfected) cells were almost all dead after two weeks, whilst between 10–30% of the cells transfected with the genes of interest remained viable. In approximately 4 weeks, enough of these viable cells were available for biological testing.

EXAMPLE 3

Testing of Newly-Established Stable Transfectants—Motility

In order to test whether the stably transfected cells (prepared according to Example 2) were different from the wild type, a technique known as the cell spreading/colony scattering assay was carried out (Jiang et al Monocyte conditioned media possess a novel factor which increases motility of cancer cells Int. J. Cancer 53 426–431 (1993)). Briefly, wild type or transfectants were plated in tissue cultureware at low density and then allowed to form colonies (clusters). These were then treated either with medium as control or with a scatter-inducing faction (HGF/SF). After 24 hours, cells were fixed and digitised images were obtained using a digital camera. The spreading and scattering were quantified as described by Jiang et al. (in Gamma linolenic acid selectively regulates the expression maspin and motility of cancer cells Biochemical and Biophysical Research Communications 237 639–644 (1997)) using an image analysis package (Optimas 6 from Optimas UK); the results for each culture were as follows:

Wild Type

Wild type MCF-7 cells formed tightly packed clusters in culture with apparent cell-cell joining. A scattering inducer (HGF/SF) can disperse the colonies, ie cells apparently move away from each other.

VC1 Transfectants

VC1 transfected cells appeared as much tighter clusters, compared with the wild type. VC1 transfectant substantially reduced their response to HGF/SF (5, 10, 2 and 50 ng/ml). Cells appeared as small, tightly-packed clusters, with cell-cell joining remaining visible.

KS2105 AND KS2101 Transfectants

KS2105 transfectant exhibited a similar cell morphology, when compared with controls. These cells, however, reduced their response significantly to HGF/SF. A similar response, although to a lesser degree, was seen with KS2101 transfectants.

KVE702 Transfectants

The established KVE702 revealed a similar morphology to control. Scattering inducer HGF/SF failed to induced a significant change. Hence, transfection did not alter the morphology of the cell, but reduced its response to HGF/SF.

Conclusion

The data obtained therefore clearly show that MCF-7 cells transfected with VC1, KS2101 and KS2105 did not significantly change their morphology. In fact, the cells appeared to reduce their response to stimulation. The data thus indicate that transfection did not alter the aggressiveness of MCF-7 cells.

EXAMPLE 4

Testing of the Recombinant Product on Angiogenesis

The study used a technique known as in vitro tubule formation analysis, to test the effect of recombinant materials on the formation of blood vessel-like structures (Kanayasu et al Eicosapentaenoic acid inhibits tube formation of vascular endothelial cells in vitro. Lipids, 26 271–276 (1991); Bach et al VE-cadherin mediates endothelial cell capillary tube formation in fibrin and collagen gels Exp Cell Res 238 324–334 (1998)).

24 multi-well plates were first coated with Matrigel™ (available from Beckton Dickinson) (200 µg/well) and allowed to form a thin gel layer. $5 \times 10^4$ HUVEC cells in 0.5 ml of DMEM with 10% foetal calf serum (FCS) were then added over Matrigel™ for 24 hours. The medium was aspirated, and a further 0.5 ml of Matrigel™ was overlaid with a further 0.5 ml of medium, which contained either medium, HGF, NK4, or NK4 and HGF in combination. Cell cultures were observed under a phase-contrast microscope after 24 hours. Each well was photographed four times at random and tubule length was measured using an image analysis software (Optimas 6 from Optimas UK). A known angiogenesis inducer, HGF/SF, and conditioned medium from the stable transfectants were then tested on the cells. The results of the study were as follows:

VC1 and KS2105 Products Reduced the Tubule Formation

Conditioned medium from the VC1 transfectant reduced the tubule forming that was induced by HGF/SF. The conditioned medium on its own appeared to have some minor effect on tubule formation. Interestingly, KS2105 supernatant reduced tubule formation both with and without angiogenesis inducer.

KVE702 Reduced Tubule Formation

Conditioned medium from KVE702 increased tubule length, although to a small degree. However, when an angiogenic factor was included, which significantly increased tubule length, KVE702 supernatant exerted a significant inhibitory effect on tubule formation. Conclusion: Therefore, it was observed that HGF/SF significantly increased tubule formation from vascular endothelial cells. Supernatants from the stable transfectants can reduce this increase in tubule formation. Hence, the present invention may present a new opportunity to produce anti-cancer agents.

EXAMPLE 5

Testing of the Recombinant Product on Invasiveness

Using the techniques described above in Example 2, MCF-7 (human breast cancer cells) were transfected with KVE702 gene and a stable transfectant selected using G418. The cells were then tested using the established Matrigel™ invasion assay described by Jiang et al in Cancer Research, 55 5043–8 (1995). It was found that the transfected cells had a reduced invasiveness compared with wild MCF-7 cells or with MCF-7 cells that had been transfected with a control plasmid carrying the Lac-z gene (available from InVitrogen). The response of the transfected cells to HGF/SF was also found to be significantly reduced, compared to wild and control cells.

Since invasiveness of cancer cells is directly related to the progression and metastasis of a cancer, its reduction indicates a potential future in cancer therapy for the recombinant product of the invention.

EXAMPLE 6

Cloning of J35 Recombinant Gene

Following the method of Example 1, the title recombinant product was prepared, using the following primers in place of i–iv of Example 1:

i   acc atg ggc gcg cag tgc acc          (SEQ ID NO: 25)

ii  ctt cag tgc tgg cac aga cgg gtc gta  (SEQ ID NO: 26)

iii tac gac ccg tct gtg cca gca ctg aag  (SEQ ID NO: 27)

iv  gac tat tgt agg tgt ggt a            (SEQ ID NO: 28)

From these reactions, the following products were generated:

1. DNA fragments were isolated from fibroblasts using RT-PCR: J9 (antagonist) (FIG. 16, [SEQ ID NO: 16]).
2. DNA fragments were isolated from HUVEC cells: J12 (endothelial marker) (FIG. 7, [SEQ ID NO: 7]).
3. A recombinant gene: A further step was carried to generate a recombinant gene, by joining J9 and J12, using the aforementioned recombinant technique. This generated a specific recombinant gene, namely: J35 (recombinant product) (FIG. 8, [SEQ ID NO: 8]).

EXAMPLE 7

Cloning of J36 Recombinant Gene

Following the method of Example 1, the title recombinant product was prepared, using the following primers in place of i–iv of Example 1:

i   acc atg gga gtg aac cca act gct cag   (SEQ ID NO: 29)

ii  ctt cag tgc tgg ctc ctg ggg atc cac   (SEQ ID NO: 30)

iii gtg gat ccc cag gag cca gca ctg aag   (SEQ ID NO: 31)

iv  gac tat tgt agg tgt ggt a             (SEQ ID NO: 28)

From these reactions, the following products were generated:
1. DNA fragments were isolated from fibroblasts using RT-PCR: J10 (antagonist) (FIG. 17, [SEQ ID NO: 17]).
2. DNA fragments were isolated from HUVEC cells: J11 (endothelial marker) (FIG. 9, [SEQ ID NO: 9])
3. A recombinant gene: A further step was carried to generate a recombinant gene, by joining KS2101 and J11, using the aforementioned recombinant technique. This generated a specific recombinant gene, namely: J36 (recombinant product) (FIG. 10, [SEQ ID NO: 10]).

EXAMPLE 8

Cloning of J37 Recombinant Gene

Following the method of Example 1, the title recombinant product was prepared, using the following primers in place of i–iv of Example 1:

i   acc atg gga gtg aac cca act gct cag   (SEQ ID NO: 29)

ii  cca aat cca atc ctc ctg gga atc cac   (SEQ ID NO: 32)

iii gtg gat ccc cag gag gat tgg att tgg   (SEQ ID NO: 33)

iv  ctg ggc ggc cat atc ctc gca gaa ggt   (SEQ ID NO: 34)

From these reactions, the following products were generated:
1. DNA fragments were isolated from fibroblasts using RT-PCR: J6 (antagonist) (FIG. 18, [SEQ ID NO: 18]).
2. DNA fragments were isolated from HUVEC cells: J8 (endothelial marker) (FIG. 11, [SEQ ID NO 11])
3. A recombinant gene: A further step was carried to generate a recombinant gene, by joining KS2101 and J8, using the aforementioned recombinant technique. This generated a specific recombinant gene, namely: J37 (recombinant product) (FIG. 10, [SEQ ID NO: 10]).

---

The invention claimed is:

1. An isolated, purified or recombinant nucleic acid sequence (hereinafter 'KV sequence') comprising: a sequence that encodes both an angiogenic factor antagonist and a vascular endothelial structure regulator, and wherein the endothelial structure regulator is selected from the group consisting of VE-cadherin, E-selectin, occludin, claudin-5 and vascular cell adhesion molecule (VCAM).

2. The isolated, purified, or recombinant nucleic acid sequence according to claim 1, comprising KVE702.

3. A vector having incorporated expressibly therein the KV sequence according to claim 1.

4. An isolated cell, plasmid, virus, or bacterium having incorporated expressibly therein the KV sequence according to claim 1.

5. An isolated host cell transfected or transformed with the vector according to claim 3.

* * * * *

SEQUENCE LISTING

<160> NUMBER OF SEQ ID NOS: 18

<210> SEQ ID NO 1
<211> LENGTH: 1695
<212> TYPE: DNA
<213> ORGANISM: Homo sapiens

<400> SEQUENCE: 1

```
atagatccag cactgaagat aaaaaccaaa aaagtgaata ctgcagacca atgtgctaat      60
agatgtacta ggaataatgg acttccattc acttgcaagg cctttgtttt tgataaagcg     120
agaaaacaat gcctctggtt ccccttcaat agcatgtcaa gtggagtgaa gaaagaattt     180
ggccatgaat ttgacctcta tgaaaacaaa gactacatta gaaactgcat catcggtaaa     240
ggacgcagct acaagggaac agtatctatc actaagagtg gcatcaaatg tcagccctgg     300
agttccatga taccacacga acacagcttt ttgccttcga gctatcgggg taaagaccta     360
caggaaaact actgtcgaaa tcctcgaggg gaagaagggg gaccctggtg tttcacaagc     420
aatccagagg tacgctacga agtctgtgac attcctcagt gttcagaagt tgaatgcatg     480
acctgcaatg gggagagtta tcgaggtctc atggatcata cagaatcagg caagatttgt     540
cagcgctggg atcatcagac accacaccgg cacaaattct tgcctgaaag atatcccgac     600
aagggctttg atgataatta ttgccgcaat cccgatggcc agccgaggcc atggtgctat     660
actcttgacc ctcacacccg ctgggagtac tgtgcaatta aaacatgcgc tgacaatact     720
gtaaatgata ctgatgttcc tatggaaaca actgaatgca tccaaggtca aggagaaggc     780
tacaggggca ctgccaatac catttggaat ggaattccat gtcagcgttg ggattctcag     840
```

```
tatcctcaca agcatgacat gactcctgaa aatttcaagt gcaaggacct acgagaaaat      900
tactgccgaa atccagatgg gtctgaatca ccctggtgtt ttaccactga tccaaacatc     960
cgagttggtt actgctccca aattccaaac tgtgatatgt caaatggaca agattgttat    1020
cgtgggaatg caaaaatta tatgggcaac ttatcccaaa caagatctgg actaacgtgt    1080
tcaatgtgga acaagaacat ggaagactta caccgtcata tcttctggga accagatgca    1140
agtaagctga atgagaatta ctgccgaaat ccagatgatg atgctcatgg accctggtgc    1200
tacacgggaa atccactcat tccttgggat tattgcccta tttctcgttg tgaaggtgat    1260
accacaccta caatagtcca gaggctcatg atgctcctcg ccacatcggg cgcctgcctg    1320
ggcctgctgg cagtggcagc agtggcagca gcaggtgcta accctgccca acgggacacc    1380
cacagcctgc tgcccaccca ccggcgccaa aagagagatt ggatttggaa ccagatgcac    1440
attgatgaag agaaaaacac ctcacttccc catcatgtag gcaagatcaa gtcaagcgtg    1500
agtcgcaaga atgccaagta cctgctcaaa ggagaatatg tgggcaaggt cttccgggtc    1560
gatgcagaga caggagacgt gttcgccatt gagaggctgg accgggagaa tatctcagag    1620
taccacctca ctgctgtcat tgtggacaag gacactggtg aaaacctgga gactccttcc    1680
agcttcacca tcaaa                                                     1695
```

<210> SEQ ID NO 2
<211> LENGTH: 566
<212> TYPE: PRT
<213> ORGANISM: Homo sapiens

<400> SEQUENCE: 2

```
Lys Ile Asp Pro Ala Leu Lys Ile Lys Thr Lys Val Asn Thr Ala
 1               5                  10                  15

Asp Gln Cys Ala Asn Arg Cys Thr Arg Asn Asn Gly Leu Pro Phe Thr
                20                  25                  30

Cys Lys Ala Phe Val Phe Asp Lys Ala Arg Lys Gln Cys Leu Trp Phe
             35                  40                  45

Pro Phe Asn Ser Met Ser Ser Gly Val Lys Lys Glu Phe Gly His Glu
         50                  55                  60

Phe Asp Leu Tyr Glu Asn Lys Asp Tyr Ile Arg Asn Cys Ile Ile Gly
 65                  70                  75                  80

Lys Gly Arg Ser Tyr Lys Gly Thr Val Ser Ile Thr Lys Ser Gly Ile
                 85                  90                  95

Lys Cys Gln Pro Trp Ser Ser Met Ile Pro His Glu His Ser Phe Leu
            100                 105                 110

Pro Ser Ser Tyr Arg Gly Lys Asp Leu Gln Glu Asn Tyr Cys Arg Asn
        115                 120                 125

Pro Arg Gly Glu Glu Gly Gly Pro Trp Cys Phe Thr Ser Asn Pro Glu
    130                 135                 140

Val Arg Tyr Glu Val Cys Asp Ile Pro Gln Cys Ser Glu Val Glu Cys
145                 150                 155                 160

Met Thr Cys Asn Gly Glu Ser Tyr Arg Gly Leu Met Asp His Thr Glu
                165                 170                 175

Ser Gly Lys Ile Cys Gln Arg Trp Asp His Gln Thr Pro His Arg His
            180                 185                 190

Lys Phe Leu Pro Glu Arg Tyr Pro Asp Lys Gly Phe Asp Asp Asn Tyr
        195                 200                 205

Cys Arg Asn Pro Asp Gly Gln Pro Arg Pro Trp Cys Tyr Thr Leu Asp
```

```
          210                 215                 220
Pro His Thr Arg Trp Glu Tyr Cys Ala Ile Lys Thr Cys Ala Asp Asn
225                 230                 235                 240

Thr Val Asn Asp Thr Asp Val Pro Met Glu Thr Thr Glu Cys Ile Gln
            245                 250                 255

Gly Gln Gly Glu Gly Tyr Arg Gly Thr Ala Asn Thr Ile Trp Asn Gly
        260                 265                 270

Ile Pro Cys Gln Arg Trp Asp Ser Gln Tyr Pro His Lys His Asp Met
            275                 280                 285

Thr Pro Glu Asn Phe Lys Cys Lys Asp Leu Arg Glu Asn Tyr Cys Arg
    290                 295                 300

Asn Pro Asp Gly Ser Glu Ser Pro Trp Cys Phe Thr Thr Asp Pro Asn
305                 310                 315                 320

Ile Arg Val Gly Tyr Cys Ser Gln Ile Pro Asn Cys Asp Met Ser Asn
                325                 330                 335

Gly Gln Asp Cys Tyr Arg Gly Asn Gly Lys Asn Tyr Met Gly Asn Leu
            340                 345                 350

Ser Gln Thr Arg Ser Gly Leu Thr Cys Ser Met Trp Asn Lys Asn Met
        355                 360                 365

Glu Asp Leu His Arg His Ile Phe Trp Glu Pro Asp Ala Ser Lys Leu
    370                 375                 380

Asn Glu Asn Tyr Cys Arg Asn Pro Asp Asp Ala His Gly Pro Trp
385                 390                 395                 400

Cys Tyr Thr Gly Asn Pro Leu Ile Pro Trp Asp Tyr Cys Pro Ile Ser
                405                 410                 415

Arg Cys Glu Gly Asp Thr Thr Pro Thr Ile Val Gln Arg Leu Met Met
            420                 425                 430

Leu Leu Ala Thr Ser Gly Ala Cys Leu Gly Leu Leu Ala Val Ala Ala
        435                 440                 445

Val Ala Ala Gly Ala Asn Pro Ala Gln Arg Asp Thr His Ser Leu
    450                 455                 460

Leu Pro Thr His Arg Arg Gln Lys Arg Asp Trp Ile Trp Asn Gln Met
465                 470                 475                 480

His Ile Asp Glu Glu Lys Asn Thr Ser Leu Pro His His Val Gly Lys
                485                 490                 495

Ile Lys Ser Ser Val Ser Arg Lys Asn Ala Lys Tyr Leu Leu Lys Gly
            500                 505                 510

Glu Tyr Val Gly Lys Val Phe Arg Val Asp Ala Glu Thr Gly Asp Val
        515                 520                 525

Phe Ala Ile Glu Arg Leu Asp Arg Glu Asn Ile Ser Glu Tyr His Leu
    530                 535                 540

Thr Ala Val Ile Val Asp Lys Asp Thr Gly Glu Asn Leu Glu Thr Pro
545                 550                 555                 560

Ser Ser Phe Thr Ile Lys
                565

<210> SEQ ID NO 3
<211> LENGTH: 1278
<212> TYPE: DNA
<213> ORGANISM: Homo sapiens

<400> SEQUENCE: 3
atagatccag cactgaagat aaaaaccaaa aaagtgaata ctgcagacca atgtgctaat    60
agatgtacta ggaataatgg acttccattc acttgcaagg cctttgtttt tgataaagcg   120
```

-continued

```
agaaaacaat gcctctggtt ccccttcaat agcatgtcaa gtggagtgaa gaaagaattt      180
ggccatgaat ttgacctcta tgaaaacaaa gactacatta gaaactgcat catcggtaaa      240
ggacgcagct acaagggaac agtatctatc actaagagtg gcatcaaatg tcagccctgg      300
agttccatga taccacacga acacagcttt tgccttcga gctatcgggg taaagaccta       360
caggaaaact actgtcgaaa tcctcgaggg gaagaagggg gaccctggtg tttcacaagc      420
aatccagagg tacgctacga agtctgtgac attcctcagt gttcagaagt tgaatgcatg      480
acctgcaatg gggagagtta tcgaggtctc atggatcata cagaatcagg caagatttgt      540
cagcgctggg atcatcagac accacaccgg cacaaattct tgcctgaaag atatcccgac      600
aagggctttg atgataatta ttgccgcaat cccgatggcc agccgaggcc atggtgctat      660
actcttgacc ctcacacccg ctgggagtac tgtgcaatta aacatgcgc tgacaatact       720 gtaaatgata ctgatgttcc tatgaaaaca actgaatgca tccaaggtca aggagaaggc      780 tacagggca ctgccaatac catttggaat ggaattccat gtcagcgttg ggattctcag       840
tatcctcaca agcatgacat gactcctgaa aatttcaagt gcaaggacct acgagaaaat     900
tactgccgaa atccagatgg gtctgaatca ccctggtgtt ttaccactga tccaaacatc     960
cgagttggtt actgctccca aattccaaac tgtgatatgt caaatggaca agattgttat    1020
cgtgggaatg gcaaaaatta tatgggcaac ttatcccaaa caagatctgg actaacgtgt    1080
tcaatgtgga acaagaacat ggaagactta caccgtcata tcttctggga accagatgca    1140
agtaagctga atgagaatta ctgccgaaat ccagatgatg atgctcatgg accctggtgc    1200
tacacgggaa atccactcat tccttgggat tattgcccta tttctcgttg tgaaggtgat    1260
accacaccta caatagtc                                                  1278

<210> SEQ ID NO 4
<211> LENGTH: 437
<212> TYPE: DNA
<213> ORGANISM: Homo sapiens

<400> SEQUENCE: 4
accacaccta caatagtcca cagaggctca tgatgctcct cgccacatcg ggcgcctgcc       60
tgggcctgct ggcagtggca gcagtggcag cagcaggtgc taaccctgcc caacgggaca      120
cccacagcct gctgcccacc caccggcgcc aaaagagaga ttggatttgg aaccagatgc      180
acattgatga agagaaaaac acctcacttc cccatcatgt aggcaagatc aagtcaagcg      240
tgagtcgcaa gaatgccaag tacctgctca aggagaata tgtgggcaag gtcttccggg      300
tcgatgcaga gacaggagac gtgttcgcca ttgagaggct ggaccgggag aatatctcag      360
agtaccacct cactgctgtc attgtggaca aggacactgg tgaaaacctg agactccttc      420
ccagcttcac catcaaa                                                    437

<210> SEQ ID NO 5
<211> LENGTH: 1287
<212> TYPE: DNA
<213> ORGANISM: Homo sapiens

<400> SEQUENCE: 5
accatgatca tagatccagc actgaagata aaaaccaaaa aagtgaatac tgcagaccaa       60
tgtgctaata gatgtactag gaataatgga cttccattca cttgcaaggc ctttgttttt     120
gataaagcga gaaaacaatg cctctggttc cccttcaata gcatgtcaag tggagtgaag     180
```

-continued

```
aaagaatttg gccatgaatt tgacctctat gaaaacaaag actacattag aaactgcatc    240
atcggtaaag gacgcagcta caagggaaca gtatctatca ctaagagtgg catcaaatgt    300
cagccctgga gttccatgat accacacgaa cacagctttt gccttcgag ctatcgggt     360 aaagacctac aggaaaacta ctgtcgaaat cctcgagggg aagaaggggg accctggtgt    420
ttcacaagca atccagaggt acgctacgaa gtctgtgaca ttcctcagtg ttcagaagtt    480
gaatgcatga cctgcaatgg ggagagttat cgaggtctca tggatcatac agaatcaggc    540
aagatttgtc agcgctggga tcatcagaca ccacaccggc acaaattctt gcctgaaaga    600
tatcccgaca agggctttga tgataattat tgccgcaatc ccgatggcca gccgaggcca    660
tggtgctata ctcttgaccc tcacacccgc tgggagtact gtgcaattaa acatgcgct     720 gacaatactg taaatgatac tgatgttcct atggaaacaa ctgaatgcat ccaaggtcaa    780
ggagaaggct acagggcac tgccaatacc atttggaatg gaattccatg tcagcgttgg    840
gattctcagt atcctcacaa gcatgacatg actcctgaaa atttcaagtg caaggaccta    900
cgagaaaatt actgccgaaa tccagatggg tctgaatcac cctggtgttt taccactgat    960
ccaaacatcc gagttggtta ctgctcccaa attccaaact gtgatatgtc aaatggacaa   1020
gattgttatc gtgggaatgg caaaaattat atgggcaact tatcccaaac aagatctgga   1080
ctaacgtgtt caatgtggaa caagaacatg gaagacttac accgtcatat cttctgggaa   1140
ccagatgcaa gtaagctgaa tgagaattac tgccgaaatc cagatgatga tgctcatgga   1200
ccctggtgct acacgggaaa tccactcatt ccttgggatt attgccctat ttctcgttgt   1260
gaaggtgata ccacacctac aatagtc                                      1287
```

```
<210> SEQ ID NO 6
<211> LENGTH: 415
<212> TYPE: DNA
<213> ORGANISM: Homo sapiens

<400> SEQUENCE: 6
gaggctcatg atgctcctcg ccacatcggg cgcctgcctg ggcctgctgg cagtggcagc     60
agtggcagca gcaggtgcta accctgccca acgggacacc cacagcctgc tgcccaccca    120
ccggcgccaa aagagagatt ggatttggaa ccagatgcac attgatgaag agaaaaacac    180
ctcacttccc catcatgtag gcaagatcaa gtcaagcgtg agtcgcaaga atgccaagta    240
cctgctcaaa ggagaatatg tgggcaaggt cttccgggtc gatgcagaga caggagacgt    300
gttcgccatt gagaggctgg accggagaa tatctcagag taccacctca ctgctgtcat    360
tgtggacaag gacactggtg aaaacctgga gactccttcc agcttcacca tcaaa         415
```

```
<210> SEQ ID NO 7
<211> LENGTH: 156
<212> TYPE: DNA
<213> ORGANISM: Homo sapiens

<400> SEQUENCE: 7
ggcgcgcagt gcaccacctg cgtggccccg ggcccggcca aggcgcgtgt ggccctcacg     60
ggaggcgtgc tctacctgtt ttgcgggctg ctggcgctcg tgccactctg ctggttcgcc    120
aacattgtcg tccgcgagtt ttacgacccg tctgtg                              156
```

```
<210> SEQ ID NO 8
<211> LENGTH: 1428
<212> TYPE: DNA
<213> ORGANISM: Homo sapiens
```

<400> SEQUENCE: 8

```
ggcgcgcagt gcaccacctg cgtggccccg ggcccggcca aggcgcgtgt ggccctcacg        60
ggaggcgtgc tctacctgtt ttgcgggctg ctggcgctcg tgccactctg ctggttcgcc       120
aacattgtcg tccgcgagtt ttacgacccg tctgtgccag cactgaagat aaaaaccaaa       180
aaagtgaata ctgcagacca atgtgctaat agatgtacta ggaataatgg acttccattc       240
acttgcaagg ccttttgtttt tgataaagcg agaaaacaat gcctctggtt ccccttcaat      300
agcatgtcaa gtggagtgaa gaagaatttt ggccatgaat ttgacctcta tgaaaacaaa       360
gactacatta gaaactgcat catcggtaaa ggacgcagct acaagggaac agtatctatc       420
actaagagtg gcatcaaatg tcagccctgg agttccatga taccacacga acacagcttt       480
ttgccttcga gctatcgggg taaagaccta caggaaaact actgtcgaaa tcctcgaggg       540
gaagaagggg gaccctggtg tttcacaagc aatccagagg tacgctacga agtctgtgac       600
attcctcagt gttcagaagt tgaatgcatg acctgcaatg gggagagtta tcgaggtctc       660
atggatcata cagaatcagg caagatttgt cagcgctggg atcatcagac accacaccgg       720
cacaaattct tgcctgaaag atatcccgac aagggctttg atgataatta tgccgcaat       780
cccgatggcc agccgaggcc atggtgctat actcttgacc ctcacacccg ctgggagtac       840
tgtgcaatta aaacatgcgc tgacaatact gtaaatgata ctgatgttcc tatggaaaca       900
actgaatgca tccaaggtca aggagaaggc tacaggggca ctgccaatac catttggaat       960
ggaattccat gtcagcgttg ggattctcag tatcctcaca gcatgacat gactcctgaa      1020
aatttcaagt gcaaggacct acgagaaaat tactgccgaa atccagatgg gtctgaatca      1080
ccctggtgtt ttaccactga tccaaacatc cgagttggtt actgctccca aattccaaac      1140
tgtgatatgt caaatggaca agattgttat cgtgggaatg gcaaaaatta tgggcaac      1200
ttatcccaaa caagatctgg actaacgtgt tcaatgtgga acaagaacat ggaagactta      1260
caccgtcata tcttctggga accagatgca agtaagctga atgagaatta ctgccgaaat      1320
ccagatgatg atgctcatgg accctggtgc tacacgggaa atccactcat tccttgggat      1380
tattgcccta tttctcgttg tgaaggtgat accacaccta caatagtc                   1428
```

<210> SEQ ID NO 9
<211> LENGTH: 144
<212> TYPE: DNA
<213> ORGANISM: Homo sapiens

<400> SEQUENCE: 9

```
ggagtgaacc caactgctca gtcttctgga tctctatatg gttcacaaat atatgccctc       60
tgcaaccaat tttatacacc tgcagctact ggactctacg tggatcagta tttgtatcac      120
tactgtgttg tggatcccca ggag                                             144
```

<210> SEQ ID NO 10
<211> LENGTH: 1416
<212> TYPE: DNA
<213> ORGANISM: Homo sapiens

<400> SEQUENCE: 10

```
ggagtgaacc caactgctca gtcttctgga tctctatatg gttcacaaat atatgccctc       60
tgcaaccaat tttatacacc tgcagctact ggactctacg tggatcagta tttgtatcac      120
tactgtgttg tggatcccca ggagccagca ctgaagataa aaaccaaaaa agtgaatact      180
```

```
gcagaccaat gtgctaatag atgtactagg aataatggac ttccattcac ttgcaaggcc      240 tttgttttg  ataaagcgag aaaacaatgc ctctggttcc ccttcaatag catgtcaagt      300
ggagtgaaga agaatttgg  ccatgaattt gacctctatg aaaacaaaga ctacattaga      360
aactgcatca tcggtaaagg acgcagctac aagggaacag tatctatcac taagagtggc      420
atcaaatgtc agccctggag ttccatgata ccacacgaac acagcttttt gccttcgagc      480
tatcggggta aagacctaca ggaaaactac tgtcgaaatc ctcgagggga agaagggga       540 ccctggtgtt tcacaagcaa tccagaggta cgctacgaag tctgtgacat tcctcagtgt      600
tcagaagtta atgcatgac  ctgcaatggg gagagttatc gaggtctcat ggatcataca      660
gaatcaggca agatttgtca gcgctgggat catcagacac cacaccggca caaattcttg      720
cctgaaagat atcccgacaa gggctttgat gataattatt gccgcaatcc cgatggccag      780
ccgaggccat ggtgctatac tcttgaccct cacacccgct gggagtactg tgcaattaaa      840
acatgcgctg acaatactgt aaatgatact gatgttccta tggaaacaac tgaatgcatc      900
caaggtcaag gagaaggcta caggggcact gccaatacca tttggaatgg aattccatgt      960
cagcgttggg attctcagta tcctcacaag catgacatga ctcctgaaaa tttcaagtgc     1020
aaggacctac gagaaaatta ctgccgaaat ccagatgggt ctgaatcacc ctggtgtttt     1080
accactgatc aaacatccg  agttggttac tgctcccaaa ttccaaactg tgatatgtca     1140
aatggacaag attgttatcg tgggaatggc aaaaattata tgggcaactt atcccaaaca     1200
agatctggac taacgtgttc aatgtggaac aagaacatgg aagacttaca ccgtcatatc     1260
ttctgggaac cagatgcaag taagctgaat gagaattact gccgaaatcc agatgatgat     1320
gctcatggac cctggtgcta cacgggaaat ccactcattc cttgggatta ttgccctatt     1380
tctcgttgtg aaggtgatac cacacctaca atagtc                              1416

<210> SEQ ID NO 11
<211> LENGTH: 150
<212> TYPE: DNA
<213> ORGANISM: Homo sapiens

<400> SEQUENCE: 11
accatgggag tgaacccaac tgctcagtct tctggatctc tatatggttc acaaatatat       60
gccctctgca accaatttta tacacctgca gctactggac tctacgtgga tcagtatttg      120
tatcactact gtgttgtgga tccccaggag                                       150

<210> SEQ ID NO 12
<211> LENGTH: 1788
<212> TYPE: DNA
<213> ORGANISM: Homo sapiens

<400> SEQUENCE: 12
accatgggag tgaacccaac tgctcagtct tctggatctc tatatggttc acaaatatat       60
gccctctgca accaatttta tacacctgca gctactggac tctacgtgga tcagtatttg      120
tatcactact gtgttgtgga tccccaggag gattggattt ggaaccagat gcacattgat      180
gaagagaaaa acacctcact tccccatcat gtaggcaaga tcaagtcaag cgtgagtcgc      240
aagaatgcca gtacctgct  caaaggagaa tatgtgggca aggtcttccg ggtcgatgca      300
gagacaggag acgtgttcgc cattgagagg ctggaccggg agaatatctc agagtaccac      360
ctcactgctg tcattgtgga caaggacact ggtgaaaacc tggagactcc ttccagcttc      420
accatcaaag ttcatgacgt gaacgacaac tggcctgtgt tcacgcatcg gttgttcaat      480
```

```
gcgtccgtgc ctgagtcgtc ggctgtgggg acctcagtca tctctgtgac agcagtggat    540
gcagacgacc ccactgtggg agaccacgcc tctgtcatgt accaaatcct gaaggggaaa    600
gagtattttg ccatcgataa ttctggacgt attatcacaa taacgaaaag cttggaccga    660
gagaagcagg ccaggtatga gatcgtggtg aagcgcgag atgcccaggg cctccggggg     720
gactcgggca cggccaccgt gctggtcact ctgcaagaca tcaatgacaa cttcccttc     780
ttcacccaga ccaagtacac atttgtcgtg cctgaagaca cccgtgtggg cacctctgtg    840
ggctctctgt tgttgagga cccagatgag ccccagaacc ggatgaccaa gtacagcatc     900
ttgcggggcg actaccagga cgctttcacc attgagacaa ccccgccca acgagggc       960
atcatcaagc ccatgaagcc tctggattat gaatacatcc agcaatacag cttcatcgtc   1020
gaggccacag accccaccat cgacctccga tacatgagcc ctcccgcggg aaacagagcc   1080
caggtcatta tcaacatcac agatgtggac gagcccccca ttttccagca gcctttctac   1140
cacttccagc tgaaggaaaa ccagaagaag cctctgattg gcacagtgct ggccatggac   1200
cctgatgcgg ctaggcatag cattggatac tccatccgca ggaccagtga caagggccag   1260
ttcttccgag tcacaaaaaa gggggacatt tacaatgaga aagaactgga cagagaagtc   1320
taccctggt ataacctgac tgtggaggcc aaagaactgg attccactgg aaccccaca    1380
ggaaaagaat ccattgtgca agtccacatt gaagttttgg atgagaatga caatgccccg   1440
gagtttgcca agccctacca gcccaaagtg tgtgagaacg ctgtccatgg ccagctggtc   1500
ctgcagatct ccgcaataga caaggacata acaccacgaa acgtgaagtt caaattcatc   1560
ttgaatactg agaacaactt taccctcacg gataatcacg ataacacggc caacatcaca   1620
gtcaagtatg ggcagtttga ccgggagcat accaaggtcc acttcctacc cgtggtcatc   1680
tcagacaatg ggatgccaag tcgcacgggc accagcacgc tgaccgtggc cgtgtgcaag   1740
tgcaacgagc agggcgagtt caccttctgc gaggatatgg ccgcccag                1788
```

<210> SEQ ID NO 13
<211> LENGTH: 482
<212> TYPE: PRT
<213> ORGANISM: Homo sapiens

<400> SEQUENCE: 13

```
Gly Ala Gln Cys Thr Thr Cys Val Ala Pro Gly Pro Ala Lys Ala Arg
 1               5                  10                  15

Val Ala Leu Thr Gly Gly Val Leu Tyr Leu Phe Cys Gly Leu Leu Ala
             20                  25                  30

Leu Val Pro Leu Cys Trp Phe Ala Asn Ile Val Arg Glu Phe Tyr
         35                  40                  45

Asp Pro Ser Val Pro Val Ser Lys Ile Asp Pro Ala Leu Lys Ile Lys
     50                  55                  60

Thr Lys Lys Val Asn Thr Ala Asp Gln Cys Ala Asn Arg Cys Thr Arg
 65                  70                  75                  80

Asn Asn Gly Leu Pro Phe Thr Cys Lys Ala Phe Val Phe Asp Lys Ala
                 85                  90                  95

Arg Lys Gln Cys Leu Trp Phe Pro Phe Asn Ser Met Ser Ser Gly Val
            100                 105                 110

Lys Lys Glu Phe Gly His Glu Phe Asp Leu Tyr Glu Asn Lys Asp Tyr
        115                 120                 125

Ile Arg Asn Cys Ile Ile Gly Lys Gly Arg Ser Tyr Lys Gly Thr Val
    130                 135                 140
```

Ser Ile Thr Lys Ser Gly Ile Lys Cys Gln Pro Trp Ser Ser Met Ile
145                 150                 155                 160

Pro His Glu His Ser Phe Leu Pro Ser Ser Tyr Arg Gly Lys Asp Leu
            165                 170                 175

Gln Glu Asn Tyr Cys Arg Asn Pro Arg Gly Glu Gly Gly Pro Trp
            180                 185                 190

Cys Phe Thr Ser Asn Pro Glu Val Arg Tyr Glu Val Cys Asp Ile Pro
            195                 200                 205

Gln Cys Ser Glu Val Glu Cys Met Thr Cys Asn Gly Glu Ser Tyr Arg
210                 215                 220

Gly Leu Met Asp His Thr Glu Ser Gly Lys Ile Cys Gln Arg Trp Asp
225                 230                 235                 240

His Gln Thr Pro His Arg His Lys Phe Leu Pro Glu Arg Tyr Pro Asp
                245                 250                 255

Lys Gly Phe Asp Asp Asn Tyr Cys Arg Asn Pro Asp Gly Gln Pro Arg
                260                 265                 270

Pro Trp Cys Tyr Thr Leu Asp Pro His Thr Arg Trp Glu Tyr Cys Ala
            275                 280                 285

Ile Lys Thr Cys Ala Asp Asn Thr Val Asn Asp Thr Asp Val Pro Met
290                 295                 300

Glu Thr Thr Glu Cys Ile Gln Gly Gln Gly Glu Gly Tyr Arg Gly Thr
305                 310                 315                 320

Ala Asn Thr Ile Trp Asn Gly Ile Pro Cys Gln Arg Trp Asp Ser Gln
                325                 330                 335

Tyr Pro His Lys His Asp Met Thr Pro Glu Asn Phe Lys Cys Lys Asp
                340                 345                 350

Leu Arg Glu Asn Tyr Cys Arg Asn Pro Asp Gly Ser Glu Ser Pro Trp
            355                 360                 365

Cys Phe Thr Thr Asp Pro Asn Ile Arg Val Gly Tyr Cys Ser Gln Ile
            370                 375                 380

Pro Asn Cys Asp Met Ser Asn Gly Gln Asp Cys Tyr Arg Gly Asn Gly
385                 390                 395                 400

Lys Asn Tyr Met Gly Asn Leu Ser Gln Thr Arg Ser Gly Leu Thr Cys
                405                 410                 415

Ser Met Trp Asn Lys Asn Met Glu Asp Leu His Arg His Ile Phe Trp
            420                 425                 430

Glu Pro Asp Ala Ser Lys Leu Asn Glu Asn Tyr Cys Arg Asn Pro Asp
            435                 440                 445

Asp Asp Ala His Gly Pro Trp Cys Tyr Thr Gly Asn Pro Leu Ile Pro
450                 455                 460

Trp Asp Tyr Cys Pro Ile Ser Arg Cys Glu Gly Asp Thr Thr Pro Thr
465                 470                 475                 480

Ile Val

<210> SEQ ID NO 14
<211> LENGTH: 475
<212> TYPE: PRT
<213> ORGANISM: Homo sapiens

<400> SEQUENCE: 14

Gly Val Asn Pro Thr Ala Gln Ser Ser Gly Ser Leu Tyr Gly Ser Gln
1               5                   10                  15

Ile Tyr Ala Leu Cys Asn Gln Phe Tyr Thr Pro Ala Ala Thr Gly Leu
            20                  25                  30

```
Tyr Val Asp Gln Tyr Leu Tyr His Tyr Cys Val Val Asp Pro Gln Glu
        35                  40                  45
Lys Ile Asp Pro Ala Leu Lys Ile Lys Thr Lys Lys Val Asn Thr Ala
    50                  55                  60
Asp Gln Cys Ala Asn Arg Cys Thr Arg Asn Asn Gly Leu Pro Phe Thr
65                  70                  75                  80
Cys Lys Ala Phe Val Phe Asp Lys Ala Arg Lys Gln Cys Leu Trp Phe
                85                  90                  95
Pro Phe Asn Ser Met Ser Ser Gly Val Lys Lys Glu Phe Gly His Glu
            100                 105                 110
Phe Asp Leu Tyr Glu Asn Lys Asp Tyr Ile Arg Asn Cys Ile Ile Gly
        115                 120                 125
Lys Gly Arg Ser Tyr Lys Gly Thr Val Ser Ile Thr Lys Ser Gly Ile
    130                 135                 140
Lys Cys Gln Pro Trp Ser Ser Met Ile Pro His Glu His Ser Phe Leu
145                 150                 155                 160
Pro Ser Ser Tyr Arg Gly Lys Asp Leu Gln Glu Asn Tyr Cys Arg Asn
                165                 170                 175
Pro Arg Gly Glu Glu Gly Gly Pro Trp Cys Phe Thr Ser Asn Pro Glu
            180                 185                 190
Val Arg Tyr Glu Val Cys Asp Ile Pro Gln Cys Ser Glu Val Glu Cys
        195                 200                 205
Met Thr Cys Asn Gly Glu Ser Tyr Arg Gly Leu Met Asp His Thr Glu
    210                 215                 220
Ser Gly Lys Ile Cys Gln Arg Trp Asp His Gln Thr Pro His Arg His
225                 230                 235                 240
Lys Phe Leu Pro Glu Arg Tyr Pro Asp Lys Gly Phe Asp Asp Asn Tyr
                245                 250                 255
Cys Arg Asn Pro Asp Gly Gln Pro Arg Pro Trp Cys Tyr Thr Leu Asp
            260                 265                 270
Pro His Thr Arg Trp Glu Tyr Cys Ala Ile Lys Thr Cys Ala Asp Asn
        275                 280                 285
Thr Val Asn Asp Thr Asp Val Pro Met Glu Thr Thr Glu Cys Ile Gln
    290                 295                 300
Gly Gln Gly Glu Gly Tyr Arg Gly Thr Ala Asn Thr Ile Trp Asn Gly
305                 310                 315                 320
Ile Pro Cys Gln Arg Trp Asp Ser Gln Tyr Pro His Lys His Asp Met
                325                 330                 335
Thr Pro Glu Asn Phe Lys Cys Lys Asp Leu Arg Glu Asn Tyr Cys Arg
            340                 345                 350
Asn Pro Asp Gly Ser Glu Ser Pro Trp Cys Phe Thr Thr Asp Pro Asn
        355                 360                 365
Ile Arg Val Gly Tyr Cys Ser Gln Ile Pro Asn Cys Asp Met Ser Asn
    370                 375                 380
Gly Gln Asp Cys Tyr Arg Gly Asn Gly Lys Asn Tyr Met Gly Asn Leu
385                 390                 395                 400
Ser Gln Thr Arg Ser Gly Leu Thr Cys Ser Met Trp Asn Lys Asn Met
                405                 410                 415
Glu Asp Leu His Arg His Ile Phe Trp Glu Pro Asp Ala Ser Lys Leu
            420                 425                 430
Asn Glu Asn Tyr Cys Arg Asn Pro Asp Asp Ala His Gly Pro Trp
        435                 440                 445
```

```
Cys Tyr Thr Gly Asn Pro Leu Ile Pro Trp Asp Tyr Cys Pro Ile Ser
    450                 455                 460

Arg Cys Glu Gly Asp Thr Thr Pro Thr Ile Val
465                 470                 475

<210> SEQ ID NO 15
<211> LENGTH: 594
<212> TYPE: PRT
<213> ORGANISM: Homo sapiens

<400> SEQUENCE: 15

Gly Val Asn Pro Thr Ala Gln Ser Ser Gly Ser Leu Tyr Gly Ser Gln
  1               5                  10                  15

Ile Tyr Ala Leu Cys Asn Gln Phe Tyr Thr Pro Ala Ala Thr Gly Leu
             20                  25                  30

Tyr Val Asp Gln Tyr Leu Tyr His Tyr Cys Val Val Asp Pro Gln Glu
         35                  40                  45

Asp Trp Ile Trp Asn Gln Met His Ile Asp Glu Lys Asn Thr Ser
     50                  55                  60

Leu Pro His His Val Gly Lys Ile Lys Ser Ser Val Ser Arg Lys Asn
 65                  70                  75                  80

Ala Lys Tyr Leu Leu Lys Gly Glu Tyr Val Gly Lys Val Phe Arg Val
                 85                  90                  95

Asp Ala Glu Thr Gly Asp Val Phe Ala Ile Glu Arg Leu Asp Arg Glu
            100                 105                 110

Asn Ile Ser Glu Tyr His Leu Thr Ala Val Ile Val Asp Lys Asp Thr
        115                 120                 125

Gly Glu Asn Leu Glu Thr Pro Ser Ser Phe Thr Ile Lys Val His Asp
    130                 135                 140

Val Asn Asp Asn Trp Pro Val Phe Thr His Arg Leu Phe Asn Ala Ser
145                 150                 155                 160

Val Pro Glu Ser Ser Ala Val Gly Thr Ser Val Ile Ser Val Thr Ala
                165                 170                 175

Val Asp Ala Asp Asp Pro Thr Val Gly Asp His Ala Ser Val Met Tyr
            180                 185                 190

Gln Ile Leu Lys Gly Lys Glu Tyr Phe Ala Ile Asp Asn Ser Gly Arg
        195                 200                 205

Ile Ile Thr Ile Thr Lys Ser Leu Asp Arg Glu Lys Gln Ala Arg Tyr
    210                 215                 220

Glu Ile Val Val Glu Ala Arg Asp Ala Gln Gly Leu Arg Gly Asp Ser
225                 230                 235                 240

Gly Thr Ala Thr Val Leu Val Thr Leu Gln Asp Ile Asn Asp Asn Phe
                245                 250                 255

Pro Phe Phe Thr Gln Thr Lys Tyr Thr Phe Val Val Pro Glu Asp Thr
            260                 265                 270

Arg Val Gly Thr Ser Val Gly Ser Leu Phe Val Glu Asp Pro Asp Glu
        275                 280                 285

Pro Gln Asn Arg Met Thr Lys Tyr Ser Ile Leu Arg Gly Asp Tyr Gln
    290                 295                 300

Asp Ala Phe Thr Ile Glu Thr Asn Pro Ala His Asn Glu Gly Ile Ile
305                 310                 315                 320

Lys Pro Met Lys Pro Leu Asp Tyr Glu Tyr Ile Gln Gln Tyr Ser Phe
                325                 330                 335

Ile Val Glu Ala Thr Asp Pro Thr Ile Asp Leu Arg Tyr Met Ser Pro
            340                 345                 350
```

-continued

```
Pro Ala Gly Asn Arg Ala Gln Val Ile Ile Asn Ile Thr Asp Val Asp
        355                 360                 365
Glu Pro Pro Ile Phe Gln Gln Pro Phe Tyr His Phe Gln Leu Lys Glu
    370                 375                 380
Asn Gln Lys Lys Pro Leu Ile Gly Thr Val Leu Ala Met Asp Pro Asp
385                 390                 395                 400
Ala Ala Arg His Ser Ile Gly Tyr Ser Ile Arg Arg Thr Ser Asp Lys
                405                 410                 415
Gly Gln Phe Phe Arg Val Thr Lys Lys Gly Asp Ile Tyr Asn Glu Lys
            420                 425                 430
Glu Leu Asp Arg Glu Val Tyr Pro Trp Tyr Asn Leu Thr Val Glu Ala
        435                 440                 445
Lys Glu Leu Asp Ser Thr Gly Thr Pro Thr Gly Lys Glu Ser Ile Val
    450                 455                 460
Gln Val His Ile Glu Val Leu Asp Glu Asn Asp Asn Ala Pro Glu Phe
465                 470                 475                 480
Ala Lys Pro Tyr Gln Pro Lys Val Cys Glu Asn Ala Val His Gly Gln
                485                 490                 495
Leu Val Leu Gln Ile Ser Ala Ile Asp Lys Asp Ile Thr Pro Arg Asn
            500                 505                 510
Val Lys Phe Lys Phe Thr Leu Asn Thr Glu Asn Asn Phe Thr Leu Thr
        515                 520                 525
Asp Asn His Asp Asn Thr Ala Asn Ile Thr Val Lys Tyr Gly Gln Phe
    530                 535                 540
Asp Arg Glu His Thr Lys Val His Phe Leu Pro Val Val Ile Ser Asp
545                 550                 555                 560
Asn Gly Met Pro Ser Arg Thr Gly Thr Ser Thr Leu Thr Val Ala Val
                565                 570                 575
Cys Lys Cys Asn Glu Gln Gly Glu Phe Thr Phe Cys Glu Asp Met Ala
            580                 585                 590
Ala Gln
```

<210> SEQ ID NO 16
<211> LENGTH: 1272
<212> TYPE: DNA
<213> ORGANISM: Homo sapiens

<400> SEQUENCE: 16

```
ccagcactga agataaaaac caaaaagtg aatactgcag accaatgtgc taatagatgt      60
actaggaata atggacttcc attcacttgc aaggcctttg ttttgataa agcgagaaaa    120
caatgcctct ggttcccctt caatagcatg tcaagtggag tgaagaaaga atttggccat   180
gaatttgacc tctatgaaaa caaagactac attagaaact gcatcatcgg taaggacgc    240
agctacaagg gaacagtatc tatcactaag agtggcatca aatgtcagcc ctggagttcc   300
atgataccac acgaacacag cttttttgcct tcgagctatc ggggtaaaga cctacaggaa   360
aactactgtc gaaatcctcg aggggaagaa gggggaccct ggtgtttcac aagcaatcca   420
gaggtacgct acgaagtctg tgacattcct cagtgttcag aagttgaatg catgacctgc   480
aatggggaga gttatcgagg tctcatggat catacagaat caggcaagat ttgtcagcgc   540
tgggatcatc agacaccaca ccggcacaaa ttcttgcctg aaagatatcc cgacaagggc   600
tttgatgata attattgccg caatcccgat ggccagccga ggccatggtg ctatactctt   660
gaccctcaca cccgctggga gtactgtgca attaaaacat gcgctgacaa tactgtaaat   720
```

| | |
|---|---|
| gatactgatg ttcctatgga aacaactgaa tgcatccaag gtcaaggaga aggctacagg | 780 |
| ggcactgcca ataccatttg aatggaatt ccatgtcagc gttgggattc tcagtatcct | 840 |
| cacaagcatg acatgactcc tgaaaatttc aagtgcaagg acctacgaga aaattactgc | 900 |
| cgaaatccag atgggtctga atcaccctgg tgttttacca ctgatccaaa catccgagtt | 960 |
| ggttactgct cccaaattcc aaactgtgat atgtcaaatg acaagattg ttatcgtggg | 1020 |
| aatggcaaaa attatatggg caacttatcc caaacaagat ctggactaac gtgttcaatg | 1080 |
| tggaacaaga acatggaaga cttacaccgt catatcttct gggaaccaga tgcaagtaag | 1140 |
| ctgaatgaga attactgccg aaatccagat gatgatgctc atggaccctg gtgctacacg | 1200 |
| ggaaatccac tcattccttg ggattattgc cctatttctc gttgtgaagg tgataccaca | 1260 |
| cctacaatag tc | 1272 |

```
<210> SEQ ID NO 17
<211> LENGTH: 1272
<212> TYPE: DNA
<213> ORGANISM: Homo sapiens

<400> SEQUENCE: 17
```

| | |
|---|---|
| ccagcactga agataaaaac caaaaaagtg aatactgcag accaatgtgc taatagatgt | 60 |
| actaggaata atggacttcc attcacttgc aaggcctttg tttttgataa agcgagaaaa | 120 |
| caatgcctct ggttcccctt caatagcatg tcaagtggag tgaagaaaga atttggccat | 180 |
| gaatttgacc tctatgaaaa caaagactac attagaaact gcatcatcgg taaggacgc | 240 |
| agctacaagg gaacagtatc tatcactaag agtggcatca aatgtcagcc ctggagttcc | 300 |
| atgataccac acgaacacag cttttttgcct tcgagctatc ggggtaaaga cctacaggaa | 360 |
| aactactgtc gaaatcctcg aggggaagaa gggggaccct ggtgtttcac aagcaatcca | 420 |
| gaggtacgct acgaagtctg tgacattcct cagtgttcag aagttgaatg catgacctgc | 480 |
| aatggggaga gttatcgagg tctcatggat catacagaat caggcaagat ttgtcagcgc | 540 |
| tgggatcatc agacaccaca ccggcacaaa ttcttgcctg aaagatatcc cgacaagggc | 600 |
| tttgatgata ttattgccg caatcccgat ggccagccga ggccatggtg ctatactctt | 660 |
| gacccctcaca cccgctggga gtactgtgca attaaaacat gcgctgacaa tactgtaaat | 720 |
| gatactgatg ttcctatgga aacaactgaa tgcatccaag gtcaaggaga aggctacagg | 780 |
| ggcactgcca ataccatttg aatggaatt ccatgtcagc gttgggattc tcagtatcct | 840 |
| cacaagcatg acatgactcc tgaaaatttc aagtgcaagg acctacgaga aaattactgc | 900 |
| cgaaatccag atgggtctga atcaccctgg tgttttacca ctgatccaaa catccgagtt | 960 |
| ggttactgct cccaaattcc aaactgtgat atgtcaaatg acaagattg ttatcgtggg | 1020 |
| aatggcaaaa attatatggg caacttatcc caaacaagat ctggactaac gtgttcaatg | 1080 |
| tggaacaaga acatggaaga cttacaccgt catatcttct gggaaccaga tgcaagtaag | 1140 |
| ctgaatgaga attactgccg aaatccagat gatgatgctc atggaccctg gtgctacacg | 1200 |
| ggaaatccac tcattccttg ggattattgc cctatttctc gttgtgaagg tgataccaca | 1260 |
| cctacaatag tc | 1272 |

```
<210> SEQ ID NO 18
<211> LENGTH: 1638
<212> TYPE: DNA
<213> ORGANISM: Homo sapiens
```

-continued

```
<400> SEQUENCE: 18
gattggattt ggaaccagat gcacattgat gaagagaaaa acacctcact tccccatcat     60
gtaggcaaga tcaagtcaag cgtgagtcgc aagaatgcca agtacctgct caaaggagaa    120
tatgtgggca aggtcttccg ggtcgatgca gagacaggag acgtgttcgc cattgagagg    180
ctggaccggg agaatatctc agagtaccac ctcactgctg tcattgtgga caaggacact    240
ggtgaaaacc tggagactcc ttccagcttc accatcaaag ttcatgacgt gaacgacaac    300
tggcctgtgt tcacgcatcg gttgttcaat gcgtccgtgc ctgagtcgtc ggctgtgggg    360
acctcagtca tctctgtgac agcagtggat gcagacgacc ccactgtggg agaccacgcc    420
tctgtcatgt accaaatcct gaaggggaaa gagtattttg ccatcgataa ttctggacgt    480
attatcacaa taacgaaaag cttggaccga gagaagcagg ccaggtatga gatcgtggtg    540
gaagcgcgag atgcccaggg cctccggggg gactcgggca cggccaccgt gctggtcact    600
ctgcaagaca tcaatgacaa cttccccttc ttcacccaga ccaagtacac atttgtcgtg    660
cctgaagaca cccgtgtggg cacctctgtg ggctctctgt ttgttgagga cccagatgag    720
ccccagaacc ggatgaccaa gtacagcatc ttgcggggcg actaccagga cgctttcacc    780
attgagacaa accccgccca caacgagggc atcatcaagc ccatgaagcc tctggattat    840
gaatacatcc agcaatacag cttcatcgtc gaggccacag accccaccat cgacctccga    900
tacatgagcc ctcccgcggg aaacagagcc caggtcatta tcaacatcac agatgtggac    960
gagcccccca ttttccagca gcctttctac cacttccagc tgaaggaaaa ccagaagaag   1020
cctctgattg gcacagtgct ggccatggac cctgatgcgg ctaggcatag cattggatac   1080
tccatccgca ggaccagtga caagggccag ttcttccgag tcacaaaaaa gggggacatt   1140
tacaatgaga aagaactgga cagagaagtc taccctggt ataacctgac tgtggaggcc    1200
aaagaactgg attccactgg aaccccccaca ggaaaagaat ccattgtgca agtccacatt   1260
gaagttttgg atgagaatga caatgccccg gagtttgcca gccctacca gcccaaagtg   1320 tgtgagaacg ctgtccatgg ccagctggtc ctgcagatct ccgcaataga caaggacata   1380
acaccacgaa acgtgaagtt caaattcatc ttgaatactg agaacaactt taccctcacg   1440
gataatcacg ataacacggc caacatcaca gtcaagtatg ggcagtttga ccgggagcat   1500
accaaggtcc acttcctacc cgtggtcatc tcagacaatg ggatgccaag tcgcacgggc   1560
accagcacgc tgaccgtggc cgtgtgcaag tgcaacgagc agggcgagtt caccttctgc   1620
gaggatatgg ccgcccag                                                 1638
```